US011433013B2

(12) United States Patent
Chung et al.

(10) Patent No.: US 11,433,013 B2
(45) Date of Patent: Sep. 6, 2022

(54) PEPTIDE FOR PREVENTING SKIN DAMAGE CAUSED BY AIR POLLUTANTS AND FOR ANTI-AGING, AND USE THEREOF

(71) Applicant: CAREGEN CO., LTD., Anyang-si (KR)

(72) Inventors: Yong Ji Chung, Seoul (KR); Eun Mi Kim, Yongin-si (KR); Eung Ji Lee, Anyang-si (KR)

(73) Assignee: CAREGEN CO., LTD., Anyang-si (KR)

( * ) Notice: Subject to any disclaimer, the term of this patent is extended or adjusted under 35 U.S.C. 154(b) by 0 days.

(21) Appl. No.: 17/059,909

(22) PCT Filed: Apr. 23, 2019

(86) PCT No.: PCT/KR2019/004881
§ 371 (c)(1),
(2) Date: Nov. 30, 2020

(87) PCT Pub. No.: WO2020/171285
PCT Pub. Date: Aug. 27, 2020

(65) Prior Publication Data
US 2021/0205200 A1 Jul. 8, 2021

(30) Foreign Application Priority Data

Feb. 20, 2019 (KR) .................. 10-2019-0020013

(51) Int. Cl.
| A61K 38/00 | (2006.01) |
| A61K 8/64 | (2006.01) |
| A61K 38/08 | (2019.01) |
| A61Q 17/00 | (2006.01) |
| A61Q 19/08 | (2006.01) |
| C07K 7/06 | (2006.01) |

(52) U.S. Cl.
CPC .............. *A61K 8/64* (2013.01); *A61K 38/08* (2013.01); *A61Q 17/00* (2013.01); *A61Q 19/08* (2013.01); *C07K 7/06* (2013.01)

(58) Field of Classification Search
CPC .......... A61K 38/08; A61K 8/64; A61Q 17/00; A61Q 19/08; C07K 7/06; A61P 11/00; A61P 17/16; A61P 35/00
See application file for complete search history.

(56) References Cited

U.S. PATENT DOCUMENTS

| 2010/0136103 | A1 | 6/2010 | Otte et al. | |
| 2013/0101662 | A1 | 4/2013 | Carreno Raima et al. | |
| 2017/0253888 | A1* | 9/2017 | Gebeyehu | C12N 9/22 |
| 2017/0319693 | A1 | 11/2017 | Koizumi et al. | |
| 2018/0237740 | A1 | 8/2018 | Kim et al. | |
| 2018/0362598 | A1* | 12/2018 | Carlson | C07K 14/325 |

FOREIGN PATENT DOCUMENTS

| KR | 10-1092915 B1 | 12/2011 |
| KR | 101092915 B1 * | 12/2011 |
| RU | 2557401 C2 | 7/2015 |
| WO | WO-2016/067628 A1 | 5/2016 |

OTHER PUBLICATIONS

Medical news today—Accessed May 8, 2020—Christina Chun, 2018 (Year: 2018).*
Robert Gale; Merck Manual accessed May 8, 2020. Overview of Cancer Therapy. (Year: 2018).*
Robert Gale; Merck Manual accessed May 8, 2020. Cancer treatment principles (Year: 2018).*
National Cancer Institute; accessed May 8, 2020. Cancer Prevention Overview (Year: 2020).*
National Cancer Institute; accessed May 8, 2020. What is Cancer? (Year: 2015).*
Achermann et al. Genetic Causes of Human Reproductive Disease. The Journal of Clinical Endocrinology & Metabolism 87(6):2447-2454 (Year: 2002).*
White et al. An Overview of the Effects of Dioxins and Dioxin-like Compounds on Vertebrates, as Documented in Human and Ecological Epidemiology. J Environ Sci Health C Environ Carcinog Ecotoxicol Rev. Oct. 2009; 27(4): 197-211 (Year: 2009).*
Landrigan et al. Environmental Pollutants and Disease in American Children: Estimates of Morbidity, Mortality, and Costs for Lead Poisoning, Asthma, Cancer, and Developmental Disabilities. Environ. Health Perspec. vol. 110:2, 2002 (Year: 2002).*
GenBank Accession No. AAM12527.1, "laminin alpha5 chain precursor [*Homo sapiens*," PRI date Sep. 16, 2020 (5 pages).
GenBank Accession No. EAW75373.1, "laminin, alpha 5, isoform CRA_b [*Homo sapiens*]," PRI date Mar. 23, 2015; (3 pages).

(Continued)

*Primary Examiner* — Aradhana Sasan
*Assistant Examiner* — Mercy H Sabila
(74) *Attorney, Agent, or Firm* — Clark & Elbing LLP; Susan M. Michaud

(57) ABSTRACT

The present invention relates to: a novel peptide having activity of preventing skin damage caused by pollutants, and skin anti-aging and wrinkle alleviation activities; and a use of the peptide, which is related to the prevention or treatment of diseases caused by pollutants or to the improvement of skin anti-aging. Particularly, the novel peptide of the present invention inhibits the inflow, into skin cells, of pollutants such as dioxin, particulate matter, and cigarette smoke, and regulates the expression of a skin aging-related gene, and thus may be effectively used as an active ingredient of a pharmaceutical composition for preventing or treating cancer, skin diseases, and lung diseases, which are caused by pollutants, or skin aging-related diseases, or as an active ingredient of a cosmetic composition for preventing skin damage caused by pollutants or for a skin anti-aging effect.

10 Claims, 12 Drawing Sheets
Specification includes a Sequence Listing.

(56) References Cited

OTHER PUBLICATIONS

GenBank Accession No. XP_024207819.1, "laminin subunit alpha-5 isoform X1 [Pan troglodytes]," PRI date Mar. 20, 2018 (5 pages).

International Search Report and Written Opinion dated Nov. 29, 2019, for PCT International Application No. PCT/KR2019/004881, Chung et al., "Peptide for Preventing Skin Damage Caused by Air Pollutants and For Anti-Aging, and Use Thereof," filed Apr. 23, 2019 (11 pages).

Office Action dated Jun. 2, 2019 for Korean Patent Application No. 10-2019-0020013, Chung et al., "Peptide for Preventing Skin Damage Caused by Air Pollutants and For Anti-Aging, and Use Thereof," filed Feb. 20, 2019 (6 pages).

Office Action dated Dec. 24, 2021, for Russian Patent Application No. 2021122392, filed Apr. 23, 2019 (partial English translation) (10 pages).

* cited by examiner

Con — 100uM 200uM
         SEQUENCE 1
              PM

Con    200uM SEQUENCE 1
              CSE

```
                        SEQUENCE LISTING

<160> NUMBER OF SEQ ID NOS: 17

<210> SEQ ID NO 1
   <211> LENGTH: 10
   <212> TYPE: PRT
   <213> ORGANISM: Artificial Sequence
   <220> FEATURE:
   <223> OTHER INFORMATION: Peptide 1

<400> SEQUENCE: 1

Ser Tyr Ser Gly Val Leu Phe Phe Leu Lys
   1               5                   10

<210> SEQ ID NO 2
   <211> LENGTH: 21
   <212> TYPE: DNA
   <213> ORGANISM: Artificial Sequence
   <220> FEATURE:
   <223> OTHER INFORMATION: CYP1A1 forward primer sequence

<400> SEQUENCE: 2
ggatctttct ctgtaccctg g                                           21

<210> SEQ ID NO 3
   <211> LENGTH: 20
   <212> TYPE: DNA
   <213> ORGANISM: Artificial Sequence
   <220> FEATURE:
   <223> OTHER INFORMATION: CYP1A1 reverse primer sequence

<400> SEQUENCE: 3
agcatgtcct tcagcccaga                                             20

<210> SEQ ID NO 4
   <211> LENGTH: 21
   <212> TYPE: DNA
   <213> ORGANISM: Artificial Sequence
   <220> FEATURE:
   <223> OTHER INFORMATION: COX-2 forward primer sequence

<400> SEQUENCE: 4
atcattcacc aggcaaattg c                                           21

<210> SEQ ID NO 5
   <211> LENGTH: 21
   <212> TYPE: DNA
   <213> ORGANISM: Artificial Sequence
   <220> FEATURE:
   <223> OTHER INFORMATION: COX-2 reverse primer sequence

<400> SEQUENCE: 5
ggcttcagca taaagcgttt g                                           21
```

```
<210> SEQ ID NO 6
<211> LENGTH: 25
<212> TYPE: DNA
<213> ORGANISM: Artificial Sequence
<220> FEATURE:
<223> OTHER INFORMATION: GAPDH forward primer sequence

<400> SEQUENCE: 6
ggtgtgaacg gatttggccg tattg                                        25

<210> SEQ ID NO 7
<211> LENGTH: 25
<212> TYPE: DNA
<213> ORGANISM: Artificial Sequence
<220> FEATURE:
<223> OTHER INFORMATION: GAPDH reverse primer sequence

<400> SEQUENCE: 7
ccgttgaatt tgccgtgagt ggagt                                        25

<210> SEQ ID NO 8
<211> LENGTH: 20
<212> TYPE: DNA
<213> ORGANISM: Artificial Sequence
<220> FEATURE:
<223> OTHER INFORMATION: SIRT1 forward primer sequence

<400> SEQUENCE: 8
tcagtggctg gaacagtgag                                              20

<210> SEQ ID NO 9
<211> LENGTH: 20
<212> TYPE: DNA
<213> ORGANISM: Artificial Sequence
<220> FEATURE:
<223> OTHER INFORMATION: SIRT1 reverse primer sequence

<400> SEQUENCE: 9
tctggcatgt cccactatca                                              20

<210> SEQ ID NO 10
<211> LENGTH: 20
<212> TYPE: DNA
<213> ORGANISM: Artificial Sequence
<220> FEATURE:
<223> OTHER INFORMATION: Col1a1 forward primer sequence

<400> SEQUENCE: 10
caccctcaag agcctgagtc                                              20

<210> SEQ ID NO 11
<211> LENGTH: 20
<212> TYPE: DNA
<213> ORGANISM: Artificial Sequence
<220> FEATURE:
<223> OTHER INFORMATION: Col1a1 reverse primer sequence

<400> SEQUENCE: 11
agacggctga gtagggaaca                                              20

<210> SEQ ID NO 12
<211> LENGTH: 20
<212> TYPE: DNA
<213> ORGANISM: Artificial Sequence
<220> FEATURE:
<223> OTHER INFORMATION: Fibronectin forward primer sequence
```

```
<400> SEQUENCE: 12
ccaggaaccg agtacaccat                                               20

<210> SEQ ID NO 13
<211> LENGTH: 20
<212> TYPE: DNA
<213> ORGANISM: Artificial Sequence
<220> FEATURE:
<223> OTHER INFORMATION: Fibronectin reverse primer sequence

<400> SEQUENCE: 13
atacccaggt tgggtgatga                                               20

<210> SEQ ID NO 14
<211> LENGTH: 20
<212> TYPE: DNA
<213> ORGANISM: Artificial Sequence
<220> FEATURE:
<223> OTHER INFORMATION: Elastin forward primer sequence

<400> SEQUENCE: 14
ggacccctga ctcgcgacct                                               20

<210> SEQ ID NO 15
<211> LENGTH: 20
<212> TYPE: DNA
<213> ORGANISM: Artificial Sequence
<220> FEATURE:
<223> OTHER INFORMATION: Elastin reverse primer sequence

<400> SEQUENCE: 15
ggggaggtgg gactgcccaa                                               20

<210> SEQ ID NO 16
<211> LENGTH: 20
<212> TYPE: DNA
<213> ORGANISM: Artificial Sequence
<220> FEATURE:
<223> OTHER INFORMATION: AQP3 forward primer sequence

<400> SEQUENCE: 16
ccttcttggg tgctggaata                                               20

<210> SEQ ID NO 17
<211> LENGTH: 20
<212> TYPE: DNA
<213> ORGANISM: Artificial Sequence
<220> FEATURE:
<223> OTHER INFORMATION: AQP3 reverse primer sequence

<400> SEQUENCE: 17
acacgataag ggaggctctg                                               20
```

PEPTIDE FOR PREVENTING SKIN DAMAGE CAUSED BY AIR POLLUTANTS AND FOR ANTI-AGING, AND USE THEREOF

SEQUENCE LISTING

The instant application contains a Sequence Listing which has been submitted electronically in ASCII format and is hereby incorporated by reference in its entirety. Said ASCII copy, created Nov. 30, 2020, is named 51401-029001_Sequence_Listing_11.30.20_ST25 and is 3,779 bytes in size.

TECHNICAL FIELD

The present invention relates to a novel peptide having activity of preventing skin damage caused by pollutants and skin anti-aging activities; and a use of the peptide.

BACKGROUND ART

In modern society, air pollution caused by the formation of large cities and industrialization has emerged as a serious social problem, and various research results have been reported that pollutants in the air may adversely affect the overall human health including the respiratory system. In particular, as the concentration of particulate matter in the air in Korea has increased significantly compared to the previous years, the media has continually reported on this matter, and thus the public interest and concern about the seriousness of air pollution have increased.

Although the respiratory system among the internal organs of the human body is most affected by pollutants in the atmosphere, but skin that directly contacts pollutants with the largest surface area and is continuously exposed to the air is one of the organs that are being the main targets of pollutants. Generally, the problem of skin health deterioration caused by the external environment has been focused on problems caused by ultraviolet rays in sunlight, but it is no longer possible to neglect the related research due to the worsening air pollution problem and increasingly pollutants in the air. There is a need for research and development of materials or cosmetics containing the same capable of protecting from air pollutants and recovering skin.

An aryl hydrocarbon receptor (AhR) is a key receptor that induces skin damage by transmitting harmful signals in cells when air pollutants come into contact with the skin. When exposed to the human skin, dioxins such as 2,3,7,8-tetrachlorodibenzo-p-dioxin (TCDD) and polyaromatic hydrocarbons (PAHs) bind to the AhR and move to the cell nucleus as in the action mechanism of steroid hormones, causing toxic mechanisms. An AhR-coupled dioxin complex binds to an AhR nuclear translocator (Arnt) protein in the nucleus, and the AhR/Arnt complex binds to a nucleotide sequence called drug/xenobiotic responsive element (DRE or XRE) in the transcriptional regulatory region of the target gene including Cytochrome P450s (P450 or cyps; CYP1A1, CYP1A2, and CYP1B1) and thus induces the transcription of several gene groups, which results in toxicity.

On the other hand, skin cells may undergo aging due to various causes, and wrinkles may occur due to aging of skin cells. The aging may be divided into chronological aging (endogenous aging), which is natural aging that occurs over time according to biological processes, and photoaging (photogenic aging), in which degenerative change occurring at the site exposed to sunlight and the chronological aging are combined. When the expression or activity of various factors related to cell growth is inhibited, natural cell aging may occur, and photoaging of skin cells may proceed by light of a wavelength in the range of 280 nm to 400 nm in sunlight. In particular, damage to skin or fibers may occur due to the irradiation of ultraviolet rays such as UVB having a wavelength in the range of 280 nm to 320 nm, and the skin may have a suntan, which may darken the skin color. UVB irradiation facilitates the accumulation of ROS and free radicals in skin cells and stimulates the intracellular signaling system by radicals, which can induce oxidative stress on biomolecules such as DNAs, proteins, and lipids, and this may cause damage to the skin tissue.

An increase in oxidative stress of skin cells may cause stimulation of keratinocytes of the epidermis or fibroblasts of the dermis, may increase the expression of genes such as matrix metalloproteinase (MMP), which is a collagen degrading enzyme, through a series of intracellular signal transduction processes, may generate a reduction in collagen that accounts 90% of the dermis as a main constituent of the skin and protects the skin from external stimuli or force by providing strength and tension to the skin, and thus skin aging or wrinkle formation may occur as a result. Therefore, effects of preventing aging of skin cells and reducing wrinkles may be expected by regulation of the expression of genes involved in the synthesis or degradation of fiber proteins such as collagen.

The aging effect of the cells caused by the irradiation of ultraviolet rays in the sunlight or the inflow of air pollutants as described above not only generates cosmetic problems according to the skin damage, but also causes serious health problems such as cancer according to the DNA damage of the cells, damage to the central and peripheral nervous system, destruction of the immune system, reproductive organ disorders, developmental disorders of infants and toddlers, and chloracne, and thus the solution of these problems is urgent.

In order to solve these problems, various materials have been developed, and there have been attempts to overcome these problems by using extracts obtained from various plants or microorganisms. In many cases, however, the exact composition of the extracts is unknown since it is not possible to specifically identify which substances in extracts from natural products can elicit effects on the protection of skin cells or recovery from aging, and thus the extract compositions containing unknown substances are being used together. Due to the characteristics of the material that should be used in direct contact with or applied to the human body, the side effects of the material should be minimized and the safety of the human body should be ensured. Therefore, a single substance having an effect that can solve the above problems needs to be accurately identified and then applied to human skin cells.

DESCRIPTION OF EMBODIMENTS

Technical Problem

Provided is a peptide that may be used for protecting skin cells by preventing skin damage caused by pollutants by inhibiting inflow of pollutants such as dioxin, particulate matter, and cigarette smoke into the cells.

Provided is a peptide that may be used for reducing an aging phenomenon of skin cells, which occurs naturally or is caused by ultraviolet rays of sunlight and thus reducing skin wrinkles.

Provided is a pharmaceutical composition for preventing or treating diseases caused by pollutants or for improving skin anti-aging by including the peptide as an active ingredient.

Provided is a cosmetic composition for preventing skin damage caused by pollutants or for improving skin anti-aging by including the peptide as an active ingredient.

Technical Solution to Problem

In order to accomplish the above object, according to an aspect of the present invention, provided is a peptide for preventing skin damage caused by pollutants, the peptide including an amino acid sequence of SEQ ID No: 1.

According to another aspect of the present invention, provided is a peptide for skin anti-aging, the peptide including an amino acid sequence of SEQ ID No: 1.

According to another aspect of the present invention, provided is a pharmaceutical composition for preventing or treating diseases caused by pollutants, the pharmaceutical composition including an amino acid sequence of SEQ ID No: 1.

According to another aspect of the present invention, provided is a pharmaceutical composition for improving skin anti-aging, the pharmaceutical composition including an amino acid sequence of SEQ ID No: 1.

According to another aspect of the present invention, provided is a cosmetic composition for preventing skin damage caused by pollutants and improving skin anti-aging, the cosmetic composition including a peptide including an amino acid sequence of SEQ ID No: 1 as an active ingredient.

Advantageous Effects of Disclosure

A peptide provided by the present invention has effects of preventing the inflow of pollutants such as dioxin, particulate matter, and cigarette smoke present in the air and inhibiting the aging phenomenon of the skin cells, and thus may be used as an active ingredient of a pharmaceutical composition for preventing or treating cancer that may be caused by pollutants, skin diseases, and lung diseases, or for decreasing skin aging, and may be used as an active ingredient of cosmetic compositions for protecting skin from pollutants and reducing skin aging and wrinkles.

However, the effects of the present invention are not limited to these effects, and effects other than those described above will clearly be understood by those skilled in the art in view of the following description.

BEST MODE

Figure 1A:
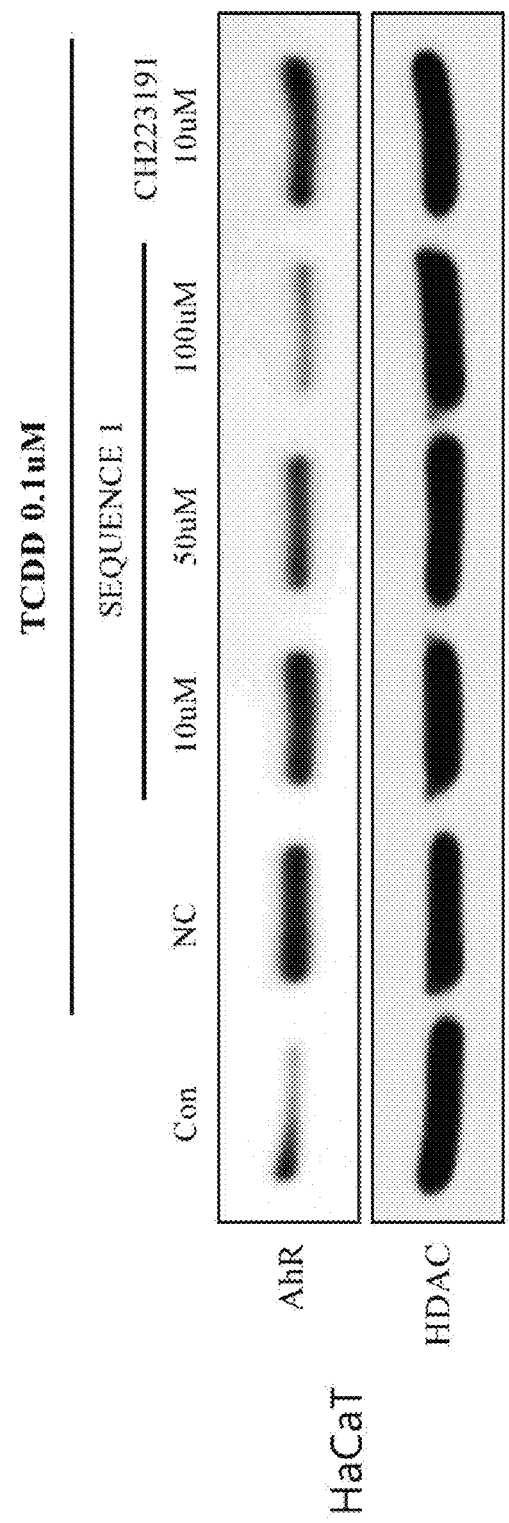
FIGS. 1A to 1C show the results of Western blotting that confirm amounts of AhR translocation to a nucleus with respect to treating HaCaT cells treated with a peptide including an amino acid sequence of SEQ ID NO: 1 with TCDD, PM, and CSE, respectively; Hereinafter, "Con" denotes control, and "NC" denotes negative control.
Figure 1B:
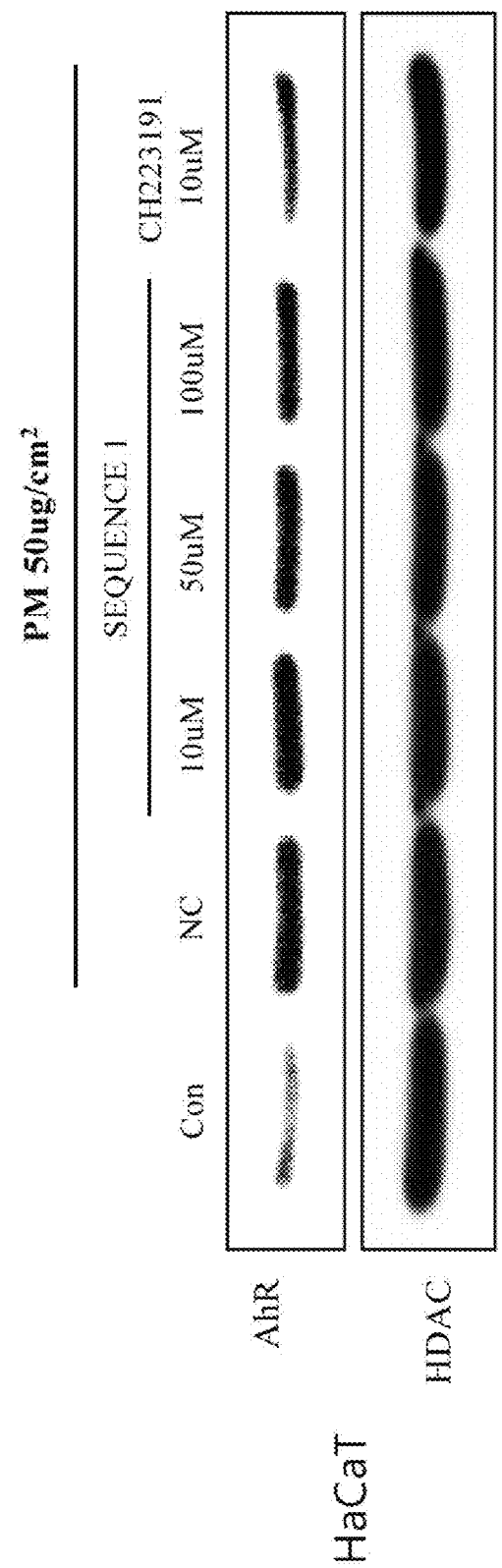
Figure 1C:
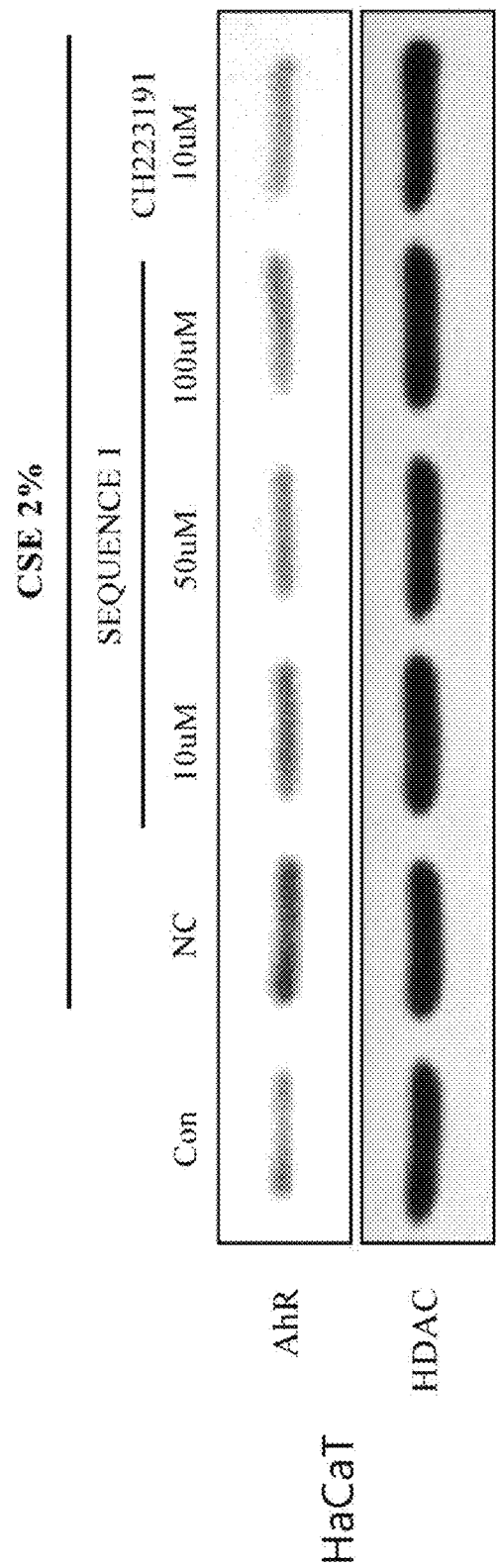
Figure 1D:
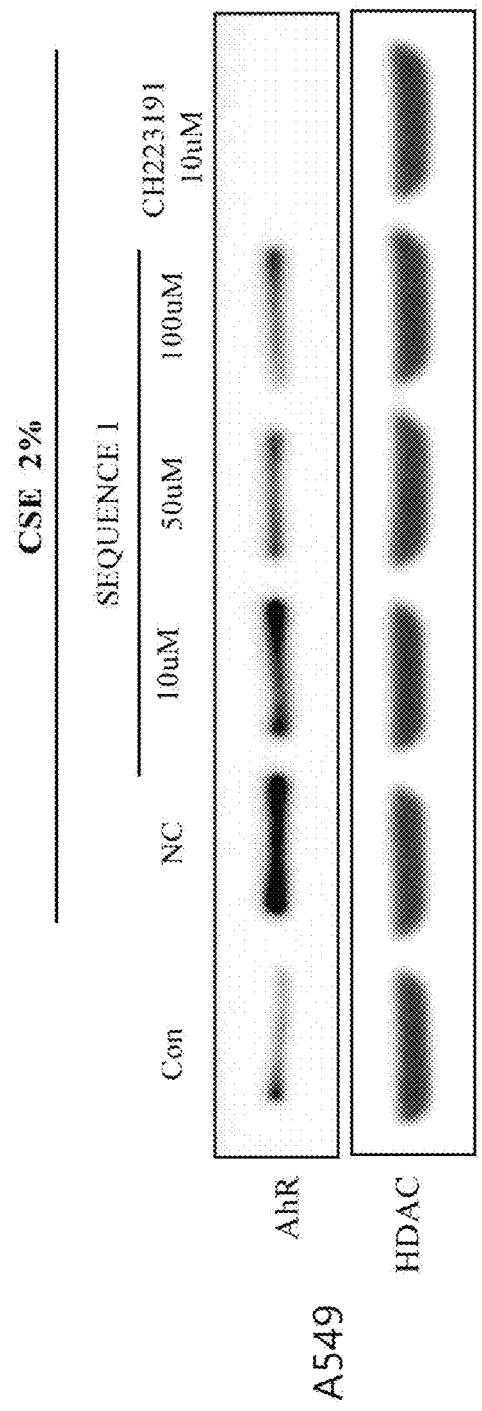
FIG. 1D shows the result of Western blotting that confirms an amount of AhR translocation to a nucleus with respect to treating A549 cells treated with a peptide including an amino acid sequence of SEQ ID NO: 1 with CSE.

Hereinafter, the present invention will be described in detail.

1. Peptide for preventing skin damage caused by pollutants or for skin anti-aging According to an aspect of the present invention, provided is a novel peptide capable of preventing skin damage caused by pollutants.

According to another aspect of the present invention, provided is a novel peptide capable of inhibiting skin aging.

The peptide refers to a polymer consisting of two or more amino acids linked by a peptide bond. The peptide is too large in self-size to effectively introduce target tissues or cells, or has a short half-life and thus disappears in the body in a short period of time. A peptide of the present invention is composed of 20 or less, for example, 15 or less, or 10 or less amino acids, which have the activity of inhibiting the entry of pollutants into cells.

The peptide of the present invention may include the amino acid sequence of SEQ ID NO: 1, and may be variants or fragments of amino acids having different sequences by deletion, insertion, substitution, or combination of amino acid residues within a range that does not affect an activity of inhibiting skin damage caused by pollutants and an anti-aging activity of the peptide. Amino acid exchange at the peptide level that does not totally modify an activity of inhibiting skin damage caused by pollutants and an anti-aging activity of the peptide is known in the art. In some cases, the peptide may be modified by phosphorylation, sulfation, acrylation, glycosylation, methylation, and farnesylation. Accordingly, the present invention includes a peptide including an amino acid sequence that is substantially identical to that of a peptide including the amino acid sequence of SEQ ID NO: 1, and a variant thereof or an active fragment thereof. The substantially identical protein refers to an amino acid sequence having 75% or more, for example, 80% or more, 90% or more, 95% or more, sequence homology with the amino acid sequence of SEQ ID NO: 1. In addition, the peptide may further include a targeting sequence, a tag, a labeled residue, a half-life, or an amino acid sequence prepared for a specific purpose to increase the stability of the peptide.

In addition, the peptide of the present invention may be obtained by various methods commonly known in the art. For example, the peptide may be prepared using polynucleotide recombination and protein expression systems, synthesis in vitro through chemical synthesis such as peptide synthesis, and cell-free protein synthesis.

In addition, in order to obtain better chemical stability, enhanced pharmacological properties (half-life, absorbency, potency, efficacy, etc.), modified specificity (e.g., a broad biological activity spectrum), and reduced antigenicity, a protective group may bind to an N- or C-terminal of the peptide. For example, the protective group may be an acetyl group, a fluorenylmethoxycarbonyl group, a formyl group, a palmitoyl group, a myristyl group, a stearyl group, or a polyethylene glycol (PEG) group, but may include any ingredient capable of enhancing modification of the peptide, particularly, stability of the peptide, without limitation. The term "stability" used in the present invention refers to storage stability (for example, room-temperature storage stability) as well as in-vivo stability that protects the peptide of the present invention from attack of a protein cleavage enzyme in vivo.

The term "pollutants" used in the present invention may refer to dioxin (TCDD), particulate matter (PM), or cigarette some extract (CSE), but embodiments are not limited thereto, and the pollutants may include any xenobiotics that enters cells from the outside and has a toxicity interfering growth and normal metabolism of the cells. Prevention of skin damage caused by pollutants may be achieved by preventing pollutants from entering the cells, thereby making it impossible for the pollutants to be toxic in the cells.

In addition, the peptide of the present invention may inhibit the inflow of pollutants into cells by adsorption with the pollutants. When pollutants such as dioxin enter the cells, they may bind to AhR to induce expression of several gene groups, and accordingly, expression of CYP1A1, CYP1A2, CYP1B1, COX-2, and MMPs may increase. In this regard, the cytoprotective effect of the peptide of the present invention through inhibition of the inflow of the pollutants into the cells may be confirmed by checking the change in the expression level of these genes.

The term "skin anti-aging" used in the present invention may refer to an effect of suppressing an aging phenomenon of skin cells. The aging may be aging that occurs naturally in cells over time, may be photoaging caused by sunlight, and in particular, may be photoaging caused by ultraviolet rays. In addition, the aging may be induced by intracellular oxidative stress phenomena that may be caused by various causes, thereby inhibiting cell growth or apoptosis, and inhibiting the synthesis of various fiber proteins constituting it in skin cells and increasing expression of degrading enzymes. In particular, when UV is irradiated, the expression of genes such as SIRT1, AQP3, Col1a1, fibronectin, and elastin are suppressed in skin cells, and the expression of MMP-1 and MMP-2 genes is promoted, which may cause photoaging and wrinkles in skin cells.

The peptides of the present invention may increase the expression of genes in pathways related to cell proliferation in skin cells, increase the expression of a fiber protein synthesis gene, or induce the suppression of the expression of a fiber proteolytic gene. Therefore, the peptide may reduce the wrinkles and improve elasticity of the skin by increasing the synthesis of fiber proteins, and has an anti-aging activity of the skin by improving the skin barrier. The effects of the peptide of the present invention improving anti-aging and reducing wrinkles in the skin may be confirmed by measuring the expression levels of genes associated with proteins involved in cell proliferation, anti-aging genes, and genes of fiber proteins and degrading enzymes thereof, where the expression levels in the skin cells change as the aging of the skin progresses.

In order to confirm the effect of preventing skin damage caused by pollutants of the peptide of the present invention, in one specific embodiment of the present invention, as a result of confirming an amount of AhR translocation to nucleus and expression levels of CYP1A1, COX-2, and MMP-1 after treating keratinocytes and fibroblasts with the peptide including an amino acid of SEQ ID NO: 1 and pollutants such as dioxin, PM, and CSE, it was confirmed that the inflow of the pollutants such as dioxin, PM, and CSE was suppressed, and thus the amount of AhR translocation to nucleus and the expression levels of CYP1A1, COX-2, and MMP-1 according to the inflow of the pollutants decreased depending on the treatment using the peptide of the present invention (see FIGS. 1A to 3B).

Figure 4A:
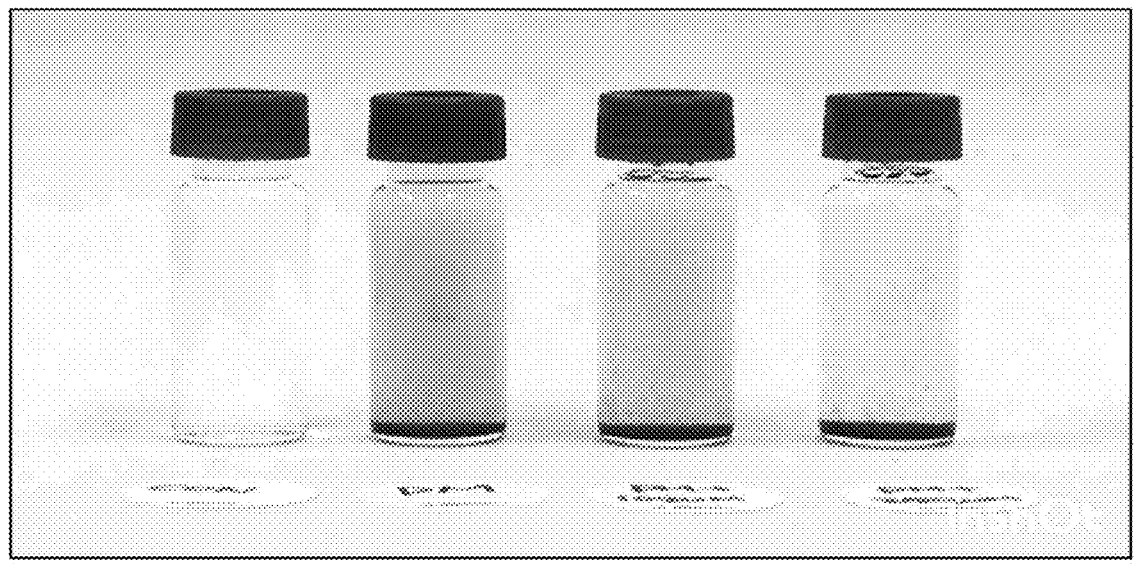
FIGS. 4A and 4B are images that confirm whether a peptide including an amino acid sequence of SEQ ID NO: 1 is precipitated by adsorption with PM and CSE, respectively.
Figure 4B:
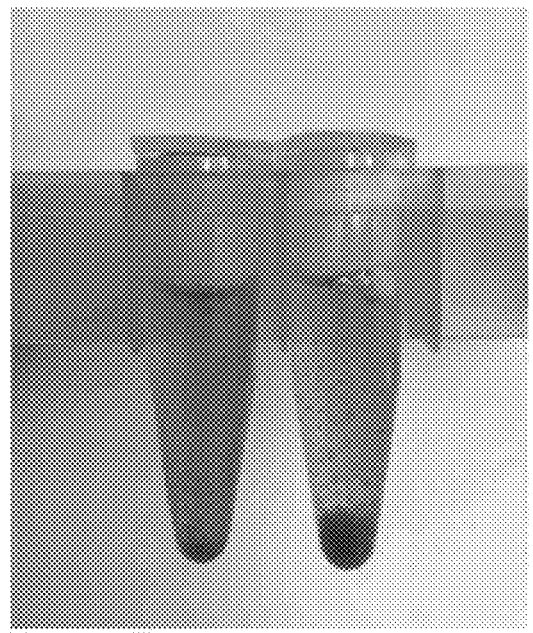

Also, in order to confirm the adsorption between the peptide and the pollutants, in another specific embodiment of the present invention, as a result of mixing PM and CSE with the peptide including an amino acid sequence of SEQ ID NO: 1 of the present invention and observing the resultant with the naked eye, it was confirmed that the peptide of the present invention was precipitated by adsorption with the pollutants such as PM and CSE and that the adsorption occurred depending on the amount of the peptide (see FIGS. 4A and 4B).

Also, in order to confirm the inhibiting effect of the peptide of the present invention on natural aging of skin cells, in another specific embodiment of the present invention, as a result of confirming amounts of phosphorylated Akt and ERK and expression levels of SIRT1, collagen, fibronectin, and elastin after treating keratinocytes and fibroblasts with the peptide including an amino acid of SEQ ID NO: 1, it was confirmed that the amounts of phosphorylated Akt and ERK, the amount of SIRT1 protein, and the expression levels of fiber proteins such as collagen, fibronectin, and elastin increased depending on the treatment using the peptide of the present invention (see FIGS. 5A to 6B).

Figure 7:
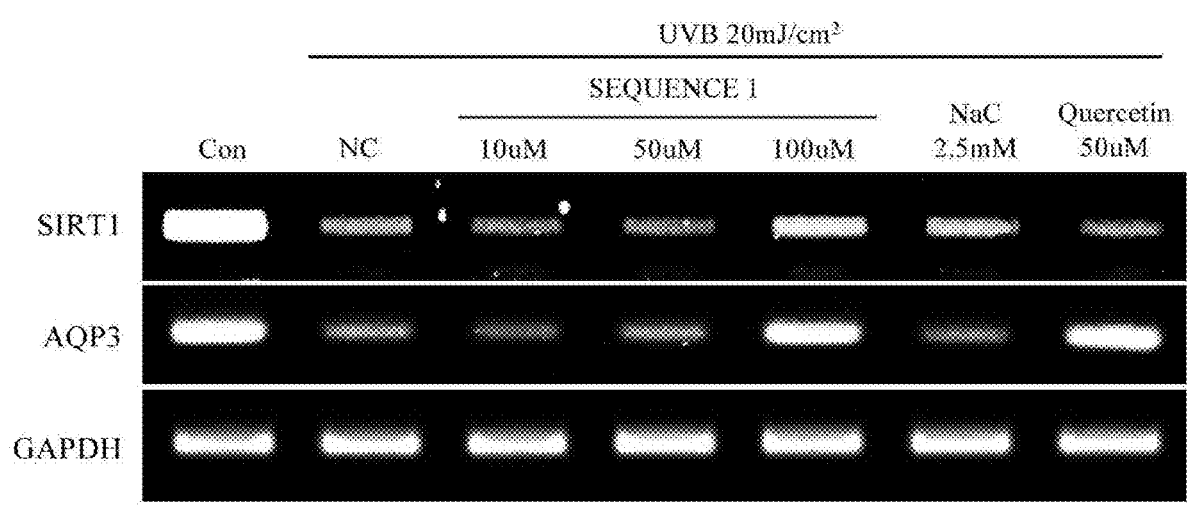
FIG. 7 shows the result of RT-PCR that confirms the expression levels of SIRT1 and AQP3 genes of HaCaT cells irradiated with UVB and treated with a peptide including an amino acid sequence of SEQ ID NO: 1.
Figure 8A:
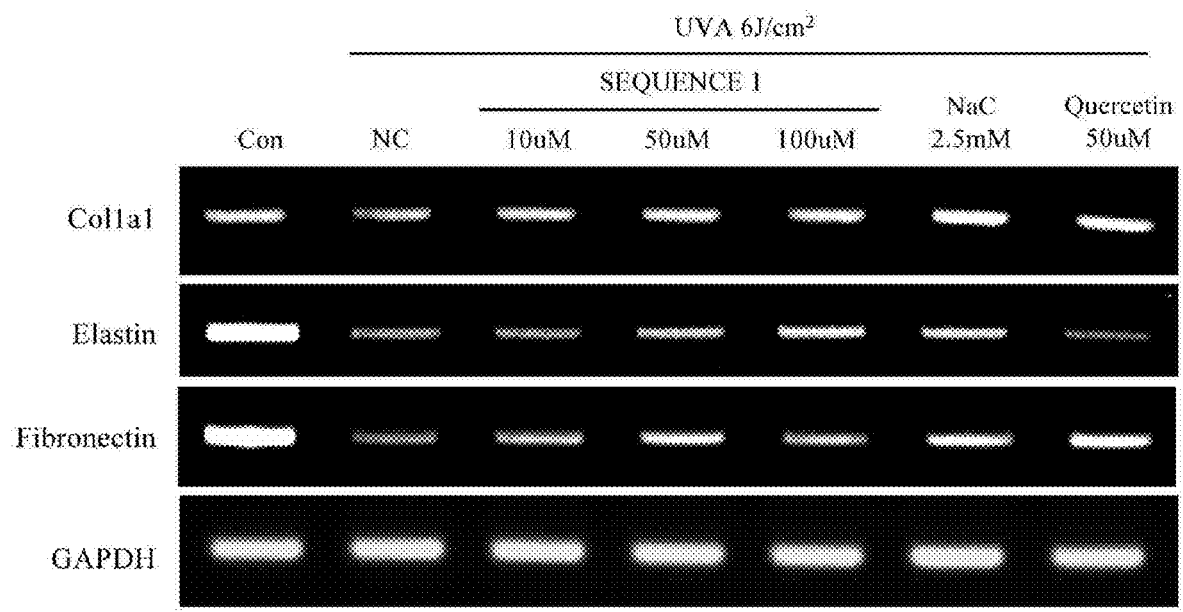
FIG. 8A shows the result of RT-PCR that confirms the expression levels of collagen (Col1a1), fibronectin, and elastin genes of NIH3T3 cells irradiated with UVB and treated with a peptide including an amino acid sequence of SEQ ID NO: 1.
Figure 8B:
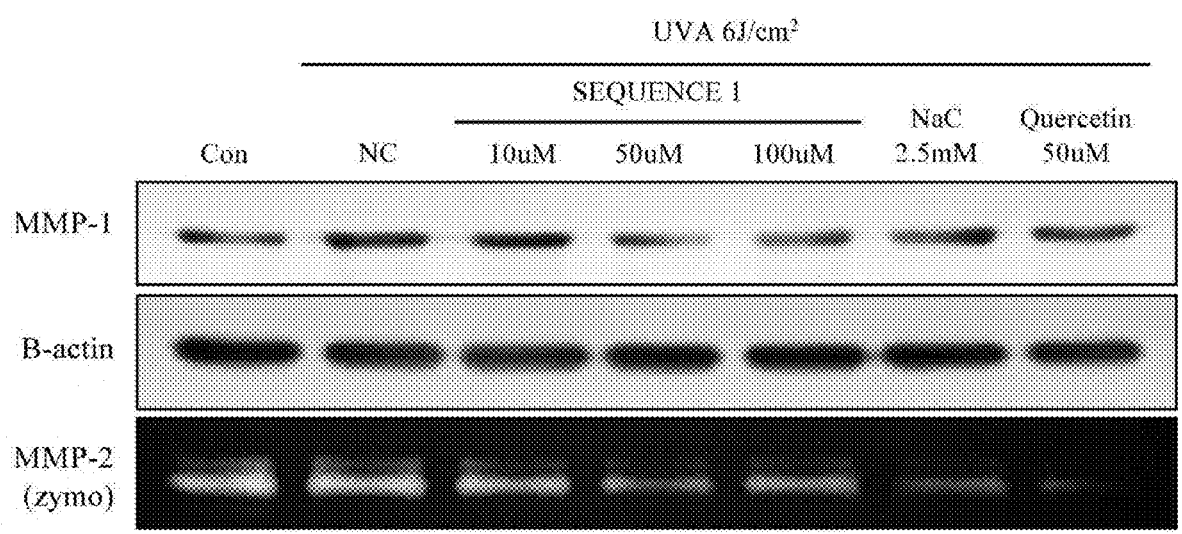
FIG. 8B shows the result of Western blotting that confirms an amount of MMP-1 protein of NIH3T3 cells irradiated with UVB and treated with a peptide including an amino acid sequence of SEQ ID NO: 1 and the result of Gelatin zymography that confirms an amount of MMP-2 protein of NIH3T3 cells irradiated with UVB and treated with a peptide including an amino acid sequence of SEQ ID NO: 1.

Also, in order to confirm the recovery effect of the peptide of the present invention from the photoaging phenomenon of skin cells according to ultraviolet (UV) irradiation, in another specific embodiment of the present invention, as a result of confirming whether decreased expression levels of SIRT1, AQP3, collagen, fibronectin, and elastin increased again and whether increased expression levels of MMP1 and MMP2 decreased again after treating keratinocytes and fibroblasts with the peptide including an amino acid of SEQ ID NO: 1, it was confirmed that the expression levels of SIRT1, AQP3, collagen, fibronectin, and elastin increased depending on the treatment using the peptide of the present invention, which confirmed recovery of the expression levels of SIRT1, AQP3, collagen, fibronectin, and elastin that had been decreased by the UV irradiation (see FIGS. 7 and 8A), and that the expression levels of MMP-1 and MMP-2 decreased depending on the treatment using the peptide of the present invention, which confirmed recovery of the expression levels of MMP-1 and MMP-2 that had been increased by the UV irradiation (see FIG. 8B).

Therefore, the peptide of the present invention prevents skin damage by inhibiting the inflow of pollutants such as TCDD, PM, and CSE into the cells and controls the expression of genes related to natural aging of skin cells or photoaging caused by ultraviolet rays, and thus it is clear that the peptide has the activity of reducing wrinkles of the skin through the anti-aging activity, and therefore, the peptide of the present invention may be effectively used as an active ingredient of a composition for preventing skin damage caused by pollutants, for anti-aging, and for reducing skin wrinkles.

2. Pharmaceutical composition for preventing or treating diseases caused by pollutants and for alleviating skin aging According to another aspect of one or more embodiments of the present invention, provided is a pharmaceutical composition for preventing or treating diseases caused by pollutants, the pharmaceutical composition including a peptide including an amino acid sequence of SEQ ID NO: 1 as an active ingredient.

According to another aspect of one or more embodiments of the present invention, provided is a pharmaceutical composition for alleviating skin aging, the pharmaceutical composition including a peptide including an amino acid sequence of SEQ ID NO: 1 as an active ingredient.

The peptide including the amino acid sequence of SEQ ID NO: 1 is the same as the peptide described in "1. Peptide for preventing skin damage caused by pollutants or for skin anti-aging", and thus the detailed description about the peptide including an amino acid sequence of SEQ ID NO: 1 may refer to the description in "1. Peptide for preventing skin damage caused by pollutants or for skin anti-aging". Hereinafter, only unique features of the pharmaceutical composition for preventing or treating diseases caused by pollutants and for alleviating skin aging will be described.

Since the peptide of the present invention is effective in inhibiting the inflow of the pollutants into cells and suppressing aging of skin cells, the pharmaceutical composition including the peptide as an active ingredient may be used to prevent or treat diseases caused by pollutants and to decrease wrinkles and increase elasticity of skin by alleviating aging of skin cells.

The diseases caused by pollutants refer to diseases caused by air pollutants such as dioxin, particulate matter, and cigarette smoke, and includes skin diseases, lung diseases, nervous system diseases, reproductive system diseases, and cardiovascular diseases, which may include cancer, atopic dermatitis, contact dermatitis, seborrheic dermatitis, acne, dry skin, psoriasis, lethality, immunotoxicity, peripheral nervous system damage, central nervous system damage, endocrine gland abnormalities, reproductive system disorders, development disorders of infants and toddlers, anemia, bronchitis, emphysema, reduced lung function, asthma, chronic bronchitis, arrhythmia, heart attack, angina, or myocardial infarction.

The pharmaceutical composition of the present invention may be used to prevent the occurrence of the diseases caused by pollutants by inhibiting the inflow of the pollutants into cells, to alleviate symptoms by suppressing additional inflow of pollutants into the cells of the patients having the diseases, and to treat diseases by inhibiting worsening of the condition.

The skin aging refers to a negative change in the skin condition that may be caused by natural aging or photoaging of skin cells. The skin aging may be physiological and/or actinic aging which include wrinkles, fine lines, reduction in skin elasticity and/or tension, crinkly, thinning, and reduction in shine and gloss of skin, may be internal skin degradation in which the dermis becomes thin as exposed to ultraviolet rays, or may be external skin degradation particularly caused by aging due to deterioration of collagen fibers.

The pharmaceutical composition of the present invention may be used to alleviate skin aging, where skin elasticity may be restored to a medically good skin condition, such as to a normal level, in relation to the skin aging naturally caused or caused by light as the pharmaceutical composition of the present invention suppresses the aging phenomenon that may occur in the skin cells.

The pharmaceutical composition containing the peptide of the present invention as an active ingredient may be formulated using a pharmaceutically acceptable carrier and/or an additive by a well-known method in the art to be prepared in a unit dose form or to be contained in a multi-dose container. Here, the formulation may be a solution in oil or an aqueous medium, a suspension, an emulsifying solution, an extract, powder, granules, a tablet, a capsule, or a gel (e.g., hydrogel), and may further include a dispersing or stabilizing agent.

Also, the peptide in the pharmaceutical composition may be carried in pharmaceutically acceptable carriers, such as colloidal suspensions, powders, saline, lipids, liposomes, microspheres, or nano spherical particles. These peptides may form or be related to a complex with a vehicle and may be carried in vivo by using carrying systems known in the art, such as lipids, liposomes, microparticles, gold, nanoparticles, polymers, condensation reagents, polysaccharides, polyamino acids, dendrimers, saponin, adsorption enhancing substances, or fatty acids.

Besides, the pharmaceutically acceptable carrier may include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil, which are generally used in preparation, but embodiments are not limited thereto. Further, the pharmaceutical composition may further include a lubricant, a wetting agent, a sweetening agent, a flavoring agent, an emulsifying agent, a suspending agent, and a preservative, in addition to the above ingredients.

The pharmaceutical composition according to the present invention may be administered orally or parenterally during clinical administration, and may be used in the form of a general pharmaceutical formulation. That is, the pharmaceutical composition of the present invention may be administered in various oral and parenteral dosage forms at the time of actual clinical administration, but when formulated, diluents or excipients such as fillers, extenders, binders, wetting agents, disintegrants, or surfactants that are commonly used in the formulation may be used. Solid preparations for oral administration may include tablets, pills, powders, granules, and capsules, and these solid preparations are formulated by mixing the herb extract or herb fermented product with at least one excipient, for example, starch, calcium carbonate, sucrose, lactose, or gelatin. Also, lubricants such as magnesium stearate or talc may be used in addition to the simple excipients. Liquid formulations for oral administrations may include suspensions, solutions, emulsions, and syrups, and the above-mentioned formulations may contain various excipients such as wetting agents, sweeteners, aromatics, and preservatives in addition to generally used simple diluents such as water and liquid paraffin. Formulations for parenteral administration may include sterilized aqueous solutions, water-insoluble excipients, suspensions, emulsions, lyophilized preparations, and suppositories. Water insoluble excipients and suspensions may include propylene glycol, polyethylene glycol, vegetable oil like olive oil, and injectable ester such as ethylolate. Suppositories may include witepsol, macrogol, tween 61, cacao butter, laurin butter, glycerol, and gelatin.

The pharmaceutical composition of the present invention is administered in a pharmaceutically effective dose. As used herein, the term "pharmaceutically effective dose" in the present invention refers to a sufficient amount to treat the diseases at a reasonable benefit/risk ratio applicable to medical treatment, and an effective dose level may be determined according to factors including the type and severity of disease of a patient, activity of a drug, sensitivity to a drug, a time of administration, a route of administration, an emission rate, duration of treatment, and simultaneously used drugs, and other factors well-known in the medical field. The pharmaceutical composition according to the present invention may be administered as a separate therapeutic agent or in combination with other therapeutic agents for diseases caused by pollutants or for alleviating skin aging, and may be administered simultaneously, separately, or sequentially with conventional therapeutic agents, and may be administered singly or multiply. It is important to administer an amount capable of obtaining a maximum effect with a minimal amount without side-effects by considering all the factors and this may be easily determined by those skilled in the art.

Particularly, the effective dose of the pharmaceutical composition of the present invention may vary depending on the age, sex, condition, and weight of a patient, absorbance of an active ingredient in vivo, an inactivation rate, an excretion rate, a disease type, and drugs to be used in combination, and may be increased or decreased according to a route of administration, the severity of obesity, sex, weight, and age. For example, the peptide of the present invention may be administered at about 0.0001 µg to 500 mg, for example, about 0.01 µg to 100 mg per kg of patient's body weight per day. In addition, the pharmaceutical composition of the present invention may be administered several times a day, for example, 2 to 3 times a day at regular time intervals according to the judgment of a doctor or pharmacist.

3. Cosmetic composition for preventing skin damage caused by pollutants or alleviating skin aging According to another aspect of the present invention, provided is a cosmetic composition for preventing skin damage caused by pollutants or alleviating skin aging, the cosmetic composition including a peptide including an amino acid of SEQ ID NO: 1.

The peptide including the amino acid sequence of SEQ ID NO: 1 is the same as the peptide described in "1. Peptide for preventing skin damage caused by pollutants or for skin anti-aging", and thus the detailed description about the peptide including an amino acid sequence of SEQ ID NO: 1 may refer to the description in "1. Peptide for preventing skin damage caused by pollutants or for skin anti-aging". Hereinafter, only unique features of the cosmetic composition for skin damage caused by pollutants or alleviating skin aging will be described.

Since the peptide of the present invention is effective in inhibiting the inflow of the pollutants into cells and suppressing aging of skin cells, the cosmetic composition including the peptide as an active ingredient may be used to prevent skin damage caused by pollutants and to decrease wrinkles and increase elasticity of skin by alleviating aging of skin cells.

The peptide may be included at an amount in a range of about 0.001 to 30 weight %, for example, about 0.1 to 20 weight %, about 0.1 to 10 weight %, about 1 to 10 weight %, or about 2 to 5 weight %, based on the total weight of 100 weight % of the cosmetic composition, but embodiments are not limited thereto.

The cosmetic composition of the present invention including the peptide as an active ingredient may, for example, include further ingredients having characteristics of enhancing activities of the peptide within a range that does not affect activities of the peptide inhibiting the inflow of pollutants into cells and alleviating skin cell aging. For example, the cosmetic composition may further include adjuvants such as fatty substances, organic solvents, solubilizers, thickening agents, gelling agents, softeners, antioxidants, suspending agents, stabilizers, foaming agents, fragrant agents, surfactants, water, ionic emulsifiers, nonionic emulsifiers, fillers, sequestering agents, chelating agents, preservatives, vitamins, blocking agents, wetting agents, essential oils, dyes, pigments, hydrophilic active agents, lipophilic active agents, lipids vesicles, or any ingredients conventionally used in cosmetics or dermatological preparations, and these components may be contained in amounts commonly used in the field of dermatology.

The cosmetic composition of the present invention may be prepared into any formulation commonly prepared in the art, and examples of the formulation may include cosmetics such as solution, suspension, emulsion, gel, lotion, essence, cream, powder, soap, shampoo, conditioner, pack mask, surfactant-containing cleanser, cleansing foam, cleansing water, oils, liquid foundation, cream foundation, or spray.

When the formulation is a solution or emulsion, a solvent, a solubilizing agent, or an emulsifying agent may be used as a carrier component, and, for example, water, ethanol, isopropanol, ethyl carbonate, ethyl acetate, benzyl alcohol, benzyl benzoate, propylene glycol, 1,3-butylglycyl oil, glycerol aliphatic ester, polyethylene glycol, or fatty acid ester of sorbitan may be used. When the formulation is a suspension, a liquid diluent such as water, ethanol or propylene glycol, an ethoxylated isostearyl alcohol, a suspending agent such as polyoxyethylene sorbitol ester and polyoxyethylene sorbitan ester, aluminum metahydroxide, microcrystalline cellulose, bentonite, agar, or tracant may be used as a carrier component. When the formulation is a cream or gel, wax, paraffin, tracant, animal oil, starch, cellulose derivatives, silicone, bentonite, polyethylene glycol, silica, zinc oxide, or talc may be used as a carrier component. When the formulation is a powder or spray, a propellant such as silica, talc, aluminum hydroxy group, lactose, calcium silicate, chlorofluorohydrocarbon, propane/butane, or dimethyl ether may be included as a carrier component. When the formulation is a surfactant-containing cleanser, aliphatic alcohol sulfate, aliphatic alcohol ether sulfate, sulfosuccinic acid monoester, imidazolinium derivative, isethionate, methyltaurate, sarcosinate, fatty acid amide ether sulfate, aliphatic alcohol, alkylamidobetaine, fatty acid glyceride, fatty acid diethanolamide, vegetable oil, lanolin derivative, or ethoxylated glycerol fatty acid ester may be used as a carrier component.

Hereinafter, the present invention will be described in more detail with reference to examples.

However, these examples illustrate the present discloser in detail, and the present invention is not limited by the following examples.

[Preparation Example] Preparation of Peptide

A peptide having an amino acid sequence of SEQ ID NO: 1 shown in Table 1 below was synthesized using an automated peptide synthesizer (Milligen 9050, available from Millipore, USA), and the synthesized peptide was isolated and purified using a C18 reverse-phase high-performance liquid chromatography (HPLC) (available from Waters Associates, USA). A column used in the HPLC was ACQUITY UPLC BEH300 C18 (2.1 mm×100 mm, 1.7 μm, available from Waters Co, USA)

TABLE 1

| SEQ ID NO: | Peptide sequence |
|---|---|
| 1 | SYSGVLFFLK |

[Experimental Example 1] Confirmation of Reduction in Amount of AhR Translocation to Nucleus According to Peptide Treatment In order to confirm an effect of inhibiting inflow of pollutants into the cells, an amount of AhR translocation to nucleus was confirmed after treating the cells with dioxin (hereinafter, also referred to as "TCDD"), particulate matter (hereinafter, also referred to as "PM"), and cigarette some extract (hereinafter, also referred to as "CSE"). When xenobiotics introduced to the cell from the outside is present, the AhR may bind with xenobiotics and act as a transcription factor and move to the nucleus in the cell, and thus an amount of inflow of pollutants into the cell may be confirmed by confirming the amount of the AhR translocation to the nucleus. Amounts of the AhR translocation to the nucleus with respect to human keratinocytes (HaCaT cells) were each confirmed after respectively treating the cells with TCDD, PM, and CSE, and an amount of AhR translocation to the nucleus with respect to human alveolar epithelial cells (A549 cells) was confirmed after treating the cells with CSE. TCDD, PM, and CSE were each used after mixing it with the peptide of the present invention and pre-reacting the mixture on a serum-free media for about 1 hour.

In order to confirm the results of the cells treated with TCDD, first, 74 passages of HaCaT cells were seeded in a 6-well plate at a cell density of $3 \times 10^5$/well and cultured for about 16 hours, and then, the culture solution was replaced with a serum-free media, and the resultant was treated with the pre-reacted mixture of TCDD and the peptide for about 1 hour. The treatment included TCDD at a concentration of about 0.1 μM and the peptide at concentrations of about 10 μM, about 50 μM, and about 100 μM, respectively. The negative control was not treated with the peptide but only treated with TCDD, and the positive control was treated with CH223191 at a concentration of about 10 μM and TCDD. After allowing the cells to react with the mixture for about 1 hour, only nucleoproteins were isolated using a kit capable of digesting cells and separating cytoplasm and nucleoproteins (Nuclear and Cytoplasmic Extraction Reagents Kit, available from Thermo scientific, USA), and then Western blotting was performed on the AhR using anti-AhR antibody (available from Santacruz biotechnology, USA) and anti-HDAC antibody (available from Santacruz biotechnology, USA). HDAC was also checked to compare the total amount of the nucleoproteins used in the experiment.

Experimental procedures of the samples treated with PM and CSE were each performed in the same manner as in the sample treated with TCDD, and the treatment included PM at a concentration of about 50 μg/cm² and CSE at a concentration of about 2%, respectively. The CSE was prepared by filling a reduced-pressure flask with 50 ml of PBS, connecting the flask to a vacuum pump, and burning 40 cigarettes. Experimental procedures for confirmation by treating the A549 cells (human alveolar epithelial cells) with CSE were similar to those of the experimental procedures described above, and 48 passages of the A549 cells were seeded in a 6-well plate at a cell density of $5 \times 10^5$/well and treated with CSE. Nucleoproteins were isolated from the resultant, and Western blotting was performed thereon.

As a result, as shown in the results of Western blotting of FIGS. 1A to 1D, when the cells were treated with the peptide, an amount of the AhR present in a nucleus decreased as a concentration of the peptide increased, compared to that of the negative control only treated with TCDD, PM, or CSE and not treated with the peptide including an amino acid sequence of SEQ ID NO: 1, where an amount of the AhR in the nucleoproteins of the cells was large.

In this regard, it may be known that the inflow of pollutants such as TCDD, PM, and CSE to HaCaT cells and A549 cells was inhibited by the peptide including an amino acid sequence of SEQ ID NO: 1, and thus the amount of AhR translocation to a nucleus also decreased.

[Experimental Example 2] Confirmation of Decrease in Expression Levels of CYP1A1 and COX-2 by Treating with Peptide In order to confirm an effect of inhibiting inflow of pollutants into the cells via another method, the cells were treated with TCDD, PM, and CSE, and expression levels of CYP1A1 and COX-2 were confirmed. When the activity of AhR is promoted by the pollutants such as TCDD, the AhR acts as a transcription factor and increases expressions of CYP1A1 and COX-2, and thus a degree of the inflow of the pollutants into the cells and whether the AhR is activated or not may be confirmed by measuring expression levels of CYP1A1 and COX-2 genes. TCDD, PM, and CSE were each used after mixing it with the peptide of the present invention and pre-reacting the mixture on a serum-free media for about 1 hour.

In order to confirm the results of the cells treated with TCDD, first, 78 passages of HaCaT cells were seeded in a 6-well plate at a cell density of $3 \times 10^5$/well and cultured for about 16 hours, and then, the culture solution was replaced with a serum-free media, and the resultant was treated with the pre-reacted mixture of TCDD and the peptide for about 2 hours. The treatment included TCDD at a concentration of about 0.1 μM and the peptide at concentrations of about 10 μM, about 50 μM, and about 100 μM, respectively. The negative control was not treated with the peptide but only treated with TCDD, and the positive control was treated with CH223191 at a concentration of about 10 μM and TCDD. The cells were reacted with the mixture for about 2 hours, and RNA was isolated from the resultant. After removing the culture solution, the plate on which the cells were cultured was treated with TRIzol (available from Thermo Fisher Scientific, USA), and a sample including RNA was obtained using a scraper. Then, the sample was treated with chloroform and centrifuged to obtain a supernatant. The supernatant was treated with isopropanol, centrifuged again, and RNA pellets at the bottom were confirmed. Next, the resultant was treated with 70% of ethanol to wash the pellets, and the pellets were sufficiently dried to isolate RNA. The isolated RNA was dissolved in RNase-free water (available from Corning, USA). The isolated RNA was reverse transcribed into cDNA, and RT-PCR (cDNA polymerization kit and PCR pre-mix, available from Intron, Korea) was performed thereon using primers of CYP1A1 and COX-2 (Table 2). A primer of GAPDH having the sequence shown in Table 2 was used for the comparison of the total RNA amounts in each of the control groups.

Experimental procedures of the samples treated with PM and CSE were each performed in the same manner as in the sample treated with TCDD, and the treatment included PM at a concentration of about 25 µg/cm$^2$ and CSE at a concentration of about 2%, respectively. The CSE was prepared by filling a reduced-pressure flask with 50 ml of PBS, connecting the flask to a vacuum pump, and burning 40 cigarettes.

TABLE 2

| SEQ ID NO: | Sequence name | Nucleotide sequence |
|---|---|---|
| 2 | CYP1A1 forward | 5'-GGATCTTTCTCTGTACCCTGG-3' |
| 3 | CYP1A1 reverse | 5'-AGCATGTCCTTCAGCCCAGA-3' |
| 4 | COX-2 forward | 5'-ATCATTCACCAGGCAAATTGC-3' |
| 5 | COX-2 reverse | 5'-GGCTTCAGCATAAAGCGTTTG-3' |
| 6 | GAPDH forward | 5'-GGTGTGAACGGATTTGGCCGTATTG-3' |
| 7 | GAPDH reverse | 5'-CCGTTGAATTTGCCGTGAGTGGAGT-3' |

Figure 2A:
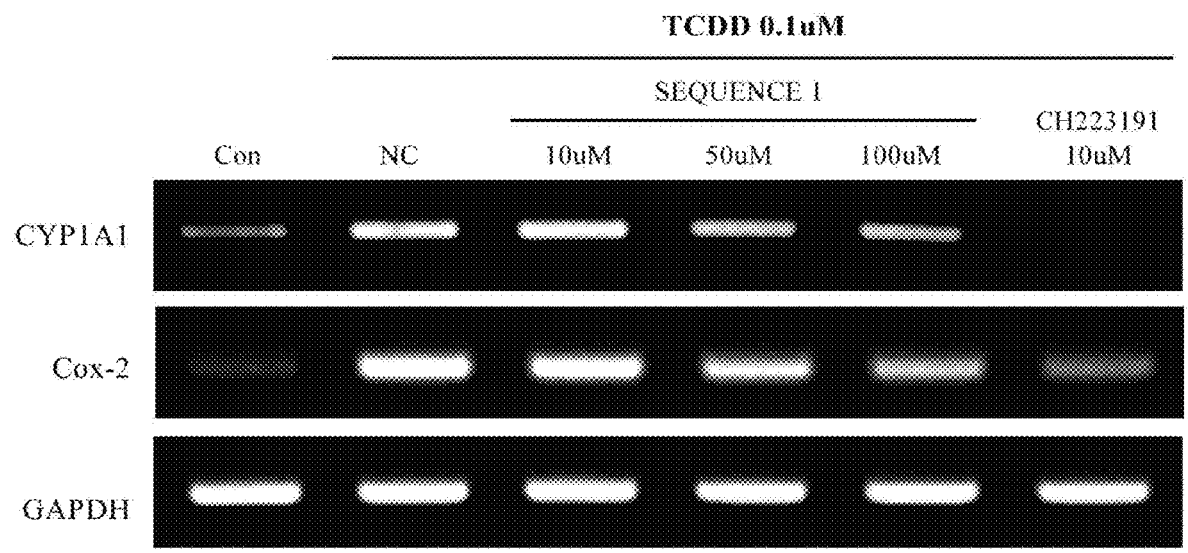
FIGS. 2A to 2C show the results of RT-PCR that confirm the expression levels of CYP1A1 and COX-2 genes with respect to treating HaCaT cells treated with a peptide including an amino acid sequence of SEQ ID NO: 1 with TCDD, PM, and CSE, respectively.
Figure 2B:
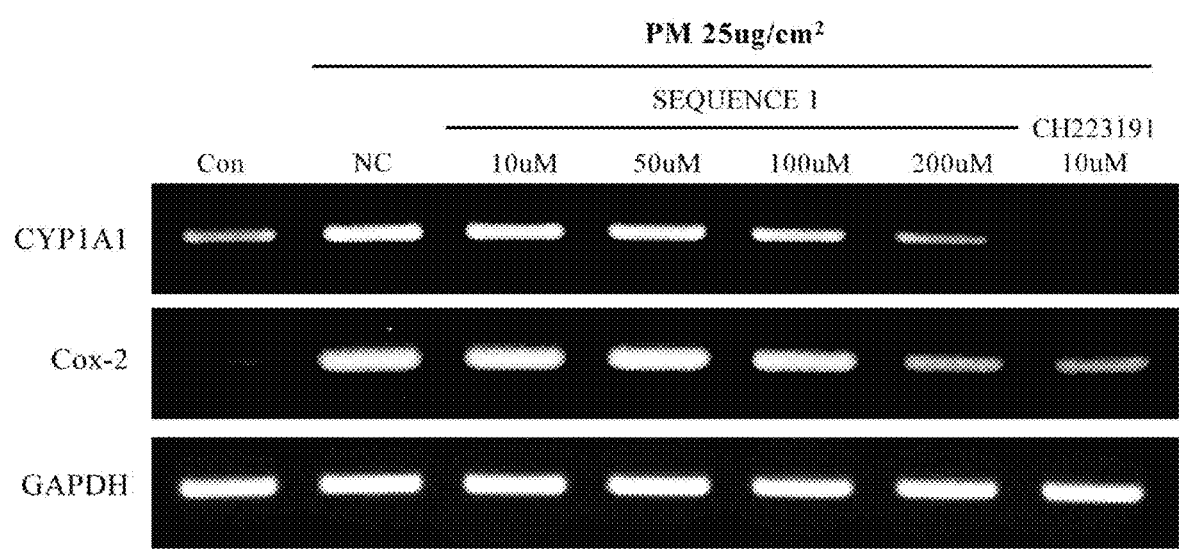
Figure 2C:
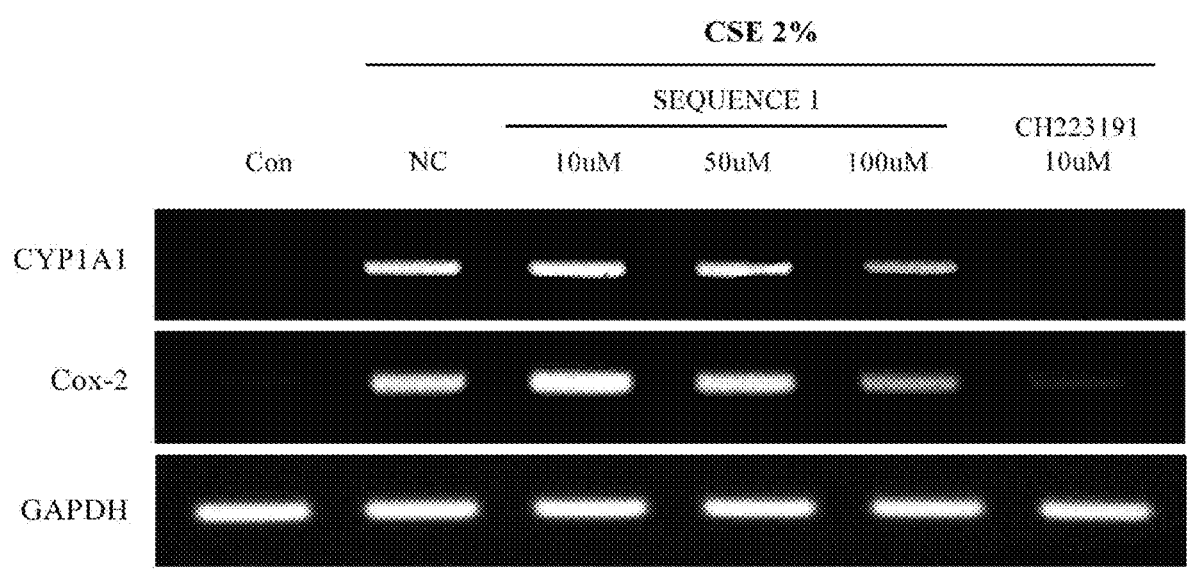

As a result, as shown in the results of RT-PCR of FIGS. 2A to 2C, when the cells were treated with the peptide, expression levels of CYP1A1 and COX-2 decreased as a concentration of the peptide increased, compared to that of the negative control only treated with TCDD, PM, or CSE and not treated with the peptide including an amino acid sequence of SEQ ID NO: 1, where expression levels of genes of CYP1A1 and COX-2 were high.

In this regard, it may be known that the inflow of pollutants such as TCDD, PM, and CSE to HaCaT cells was inhibited by the peptide including an amino acid sequence of SEQ ID NO: 1, and thus the expression levels of CYP1A1 and COX-2 also decreased.

[Experimental Example 3] Confirmation of Decrease in Amounts of MMP-1 and COX-2 Proteins by Treating with Peptide HaCaT cells were treated with TCDD and PM, and amounts of MMP-1 and COX-2 proteins were measured to confirm an effect of inhibiting inflow of pollutants into the cells via another method. The MMP-1 is a collagenase. When the activity of AhR is promoted by the pollutants such as TCDD, the AhR acts as a transcription factor and increases expressions of MMP-1 and COX-2, and thus a degree of the inflow of the pollutants into the cells and whether the AhR is activated or not may be confirmed by measuring expression levels of MMP-1 and COX-2 genes. TCDD and PM were each used after mixing it with the peptide of the present invention and pre-reacting the mixture on a serum-free media for about 1 hour.

In order to confirm the results of the cells treated with TCDD, first, 80 passages of HaCaT cells were seeded in a 6-well plate at a cell density of 3×10$^5$/well and cultured for about 16 hours, and then, the culture solution was replaced with a serum-free media, and the resultant was treated with the pre-reacted mixture of TCDD and the peptide for about 24 hours. The treatment included TCDD at a concentration of about 0.1 µM and the peptide at concentrations of about 10 µM, about 50 µM, and about 100 µM, respectively. The negative control was not treated with the peptide but only treated with TCDD, and the positive control was treated with CH223191 at a concentration of about 10 µM and TCDD. After allowing the cells to react with the mixture for about 24 hours, a lysate was obtained from the cells, and then Western blotting was performed on the MMP-1 and COX-2 using anti-MMP-1 antibody (available from Cell Signaling, USA) and anti-COX-2 antibody (available from Santacruz biotechnology, USA).

β-actin used in the test was anti-β-actin antibody (available from Santacruz biotechnology, USA) to compare the total amounts of proteins.

Experimental procedures of the sample treated with PM were each performed in the same manner as in the sample treated with TCDD, and the treatment included PM at a concentration of about 50 µg/cm$^2$.

Figure 3A:
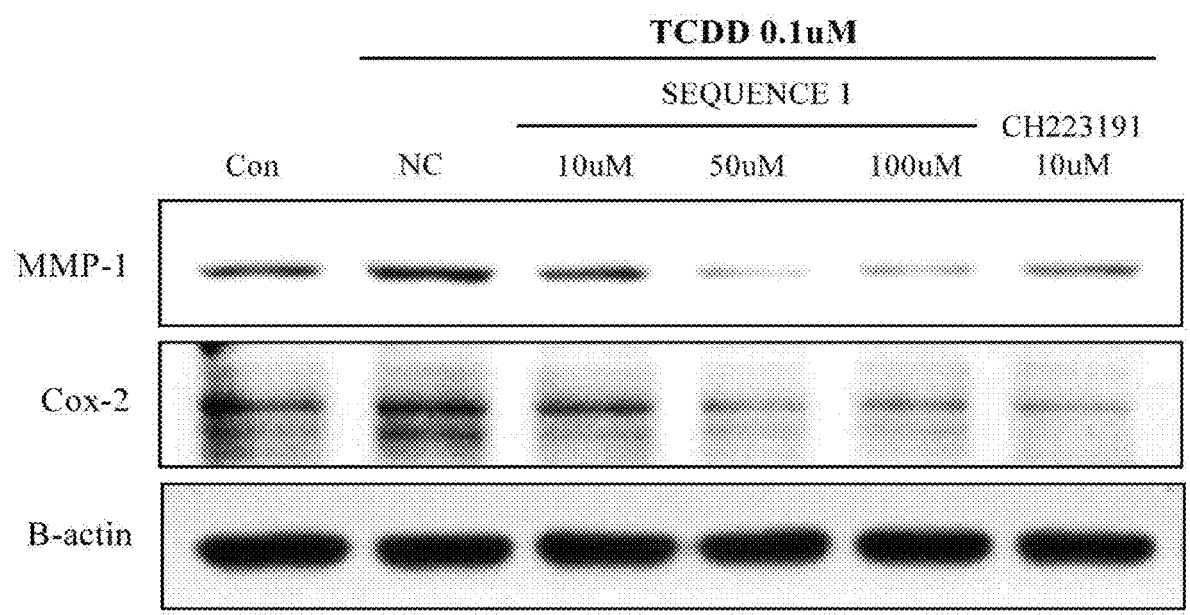
FIGS. 3A and 3B show the results of Western blotting that confirm amounts of MMP-1 and COX-2 proteins with respect to treating HaCaT cells treated with a peptide including an amino acid sequence of SEQ ID NO: 1 with TCDD and PM, respectively.
Figure 3B:
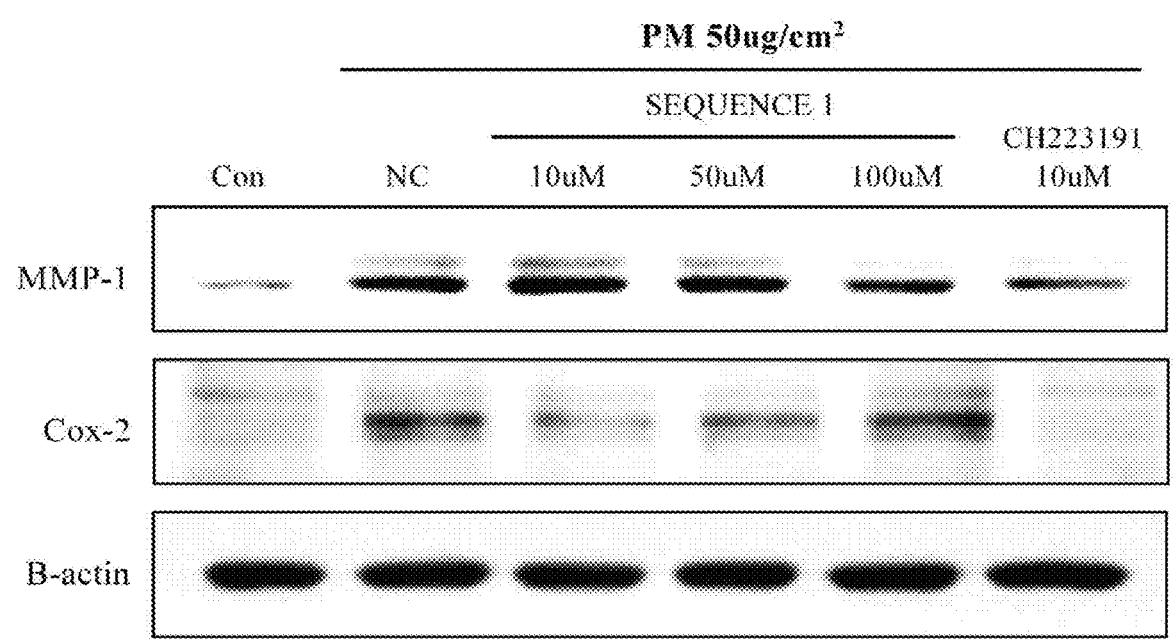

As a result, as shown in the results of Western blotting of FIGS. 3A and 3B, when the cells were treated with the peptide, amounts of the MMP-1 and COX-2 proteins decreased as a concentration of the peptide increased, compared to that of the negative control only treated with TCDD or PM and not treated with the peptide including an amino acid sequence of SEQ ID NO: 1, where amounts of the MMP-1 and COX-2 proteins were large.

In this regard, it may be known that the inflow of pollutants such as TCDD and PM to HaCaT cells was inhibited by the peptide including an amino acid sequence of SEQ ID NO: 1, and thus the amounts of the MMP-1 and COX-2 proteins also decreased.

[Experimental Example 4] Confirmation of Adsorbing Effect of Peptide with Environmental Pollutants A pattern of precipitation of the mixture of the peptide and pollutants was observed with the naked eye to confirm whether the peptide of the present invention is adsorbed with pollutants.

First, to confirm a degree of adsorption of particulate matter, 100 µg/ml of PM and each of 100 µM and 200 µM the peptide were mixed to observe the pattern of precipitation, and CSE prepared using the smoke of 40 cigarettes and 200 µM the peptide were mixed and observed with the naked eye.

As a result, as shown in the results of FIGS. 4A and 4B, when the cells were treated with the peptide, a degree of gradual precipitation sinking downward increased as a concentration of the peptide increased, compared to that of the cells only treated with PM or CSE and not treated with the peptide including an amino acid sequence of SEQ ID NO: 1, where the PM and CSE remained present in the mixture.

In this regard, it may be known that the peptide including an amino acid sequence of SEQ ID NO: 1 catches and adsorbs molecules of the pollutants such as PM or CSE, and thus there is an effect of inhibiting the inflow of the molecules of the pollutants into the skin.

[Experimental Example 5] Confirmation of Promoting Activity of Keratinocytes by Treating with Natural Aging-Inhibiting Peptide Amounts of proteins and expression levels of genes involved in natural aging were measured to confirm whether the peptide of the present invention may inhibit a cell aging phenomenon naturally progressing in the cells, with respect to keratinocytes.

<5-1> Confirmation of Phosphorylation of Proliferation-Related Signaling Proteins Since Akt and ERK are proteins involved in the signal transduction process related to cell proliferation, and exhibit activity in their phosphorylated forms (p-Akt and p-ERK, respectively), whether the increase in phosphorylated Akt and ERK may suppress the phenomenon of cell aging or not when the cells are treated with the peptide of the present invention was confirmed.

First, 81 passages of HaCaT cells were seeded in a 6-well plate at a cell density of $3 \times 10^5$/well and cultured for about 24 hours, and then, the cells were treated with the peptide of the present invention at concentrations of 10 μM, 50 μM, and 100 μM, respectively, for about 15 minutes. The positive control was treated with growth factors, 100 nM of bFGF and 100 nM of IGF, respectively, instead of the peptide. After allowing the cells to react with the mixture for about 15 minutes, a lysate was obtained from the cells, and then Western blotting was performed on the p-Akt and p-ERK using anti-p-Akt antibody (available from Cell Signaling, USA) and anti-p-ERK antibody (available from Cell Signaling, USA).

β-actin used in the test was anti-β-actin antibody (available from Santacruz biotechnology, USA) to compare the total amounts of proteins.

Figure 5A:
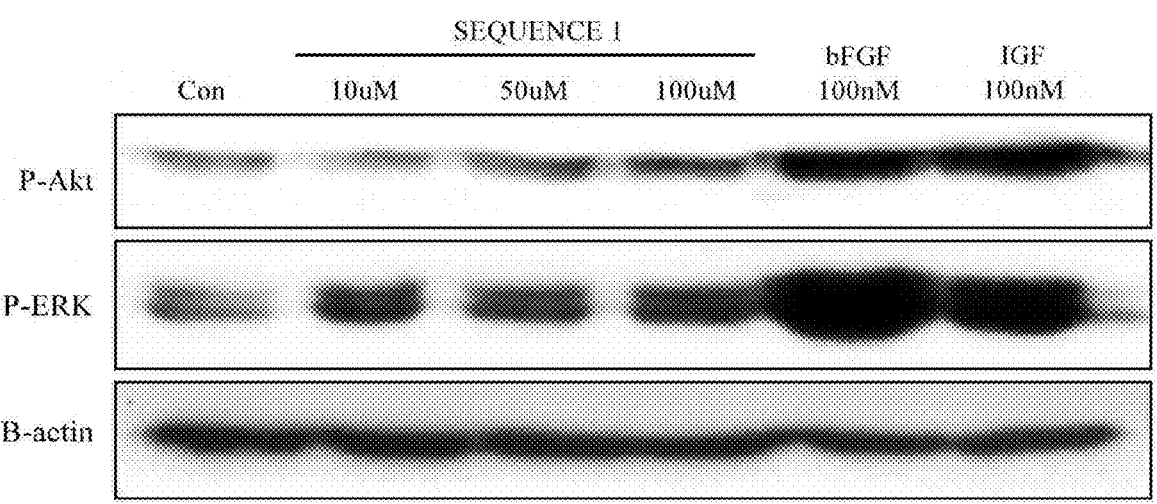
FIG. 5A shows the result of Western blotting that confirms amounts of p-Akt and p-ERK proteins of HaCaT cells treated with a peptide including an amino acid sequence of SEQ ID NO: 1.

As a result, as shown in the result of the Western blotting of FIG. 5A, it was confirmed that phosphorylation degrees of Akt and ERK gradually increased as the concentration of the peptide increased when the cells were treated with the peptide.

In this regard, the phosphorylation degrees of Akt and ERK in the HaCaT cells increased by the peptide including an amino acid sequence of SEQ ID NO: 1, which denotes promotion of growth of the cells, and thus it may be known that a natural aging phenomenon may be suppressed by treating the cells with the peptide.

<5-2> Confirmation of Increase in Expression of SIRT1 (Anti-Aging Gene)

Whether a cell aging phenomenon may be suppressed by treating the cells with the peptide of the present invention was confirmed by checking whether an expression level of SIRT1 gene, which prevents aging, increases or not.

78 passages of HaCaT cells were seeded in a 6-well plate at a cell density of $3 \times 10^5$/well and cultured for about 24 hours, and then, the cells were treated with the peptide of the present invention at concentrations of 10 μM, 50 μM, and 100 μM, respectively, for about 24 hours. The positive control was treated with growth factors, 100 nM of bFGF and 100 nM of IGF, respectively, instead of the peptide. After allowing the cells to react with the mixture for about 24 hours, RNA was isolated from the cells in the same manner as in Experimental Example 2, and the isolated RNA was reverse transcribed into cDNA, and RT-PCR (cDNA polymerization kit and PCR pre-mix, available from Intron, Korea) was performed thereon using a primer of SIRT1 (Table 3). A primer of GAPDH having the sequence shown in Table 2 was used for the comparison of the total RNA amounts in each of the control groups.

TABLE 3

| SEQ ID NO: | Sequence name | Nucleotide sequence |
|---|---|---|
| 8 | SIRT1 forward | 5'-TCAGTGGCTGGAACAGTGAG-3' |
| 9 | SIRT1 reverse | 5'-TCTGGCATGTCCCACTATCA-3' |

Figure 5B:
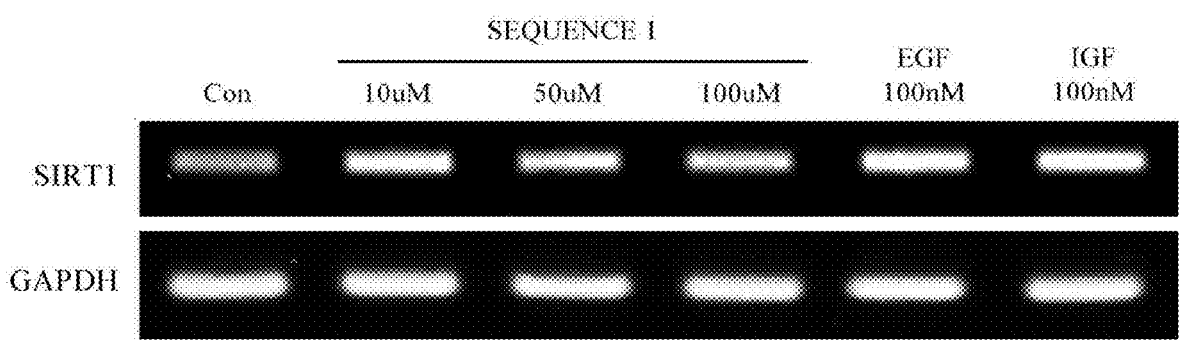
FIG. 5B shows the result of RT-PCR that confirms the expression levels of SIRT1 gene of HaCaT cells treated with a peptide including an amino acid sequence of SEQ ID NO: 1.

As a result, as shown in the result of RT-PCR of FIG. 5B, it was confirmed that an expression level of SIRT1 gene increased as the concentration of the peptide increased when the cells were treated with the peptide.

In this regard, it may be known that the expression level of SIRT1 gene, which is an anti-aging gene, increased in the HaCaT cells by the peptide including an amino acid sequence of SEQ ID NO: 1, and thus a natural aging phenomenon of the cells may be suppressed.

[Experimental Example 6] Confirmation of Activity Promotion of Fibroblasts by Treating with Natural Aging-Inhibiting Peptide Amounts of proteins and expression levels of genes involved in natural aging were measured to confirm whether the peptide of the present invention may suppress a cell aging phenomenon naturally progressing in the cells, with respect to fibroblasts.

<6-1> Confirmation of Phosphorylation of Proliferation-Related Signal Proteins

Since Akt and ERK are proteins involved in the signal transduction process related to cell proliferation, and exhibit activity in their phosphorylated forms (p-Akt and p-ERK, respectively), whether the increase in phosphorylated Akt and ERK in cells may suppress the phenomenon of cell aging when the cells are treated with the peptide of the present invention was confirmed.

First, 38 passages of NIH3T3 cells (mouse fibroblasts) were seeded in a 6-well plate at a cell density of $3 \times 10^5$/well and cultured for about 24 hours in a serum free media, and then, the cells were treated with the peptide of the present invention at concentrations of 10 μM, 50 μM, and 100 μM, respectively, for about 15 minutes. The positive control was treated with growth factors, 50 nM of bFGF and 25 nM of IGF, respectively, instead of the peptide. After allowing the cells to react with the mixture for about 15 minutes, a lysate was obtained from the cells, and then Western blotting was performed on the p-Akt and p-ERK using anti-p-Akt antibody (available from Cell Signaling, USA) and anti-p-ERK antibody (available from Cell Signaling, USA). β-actin used in the test was anti-β-actin antibody (available from Santacruz biotechnology, USA) to compare the total amounts of proteins.

Figure 6A:
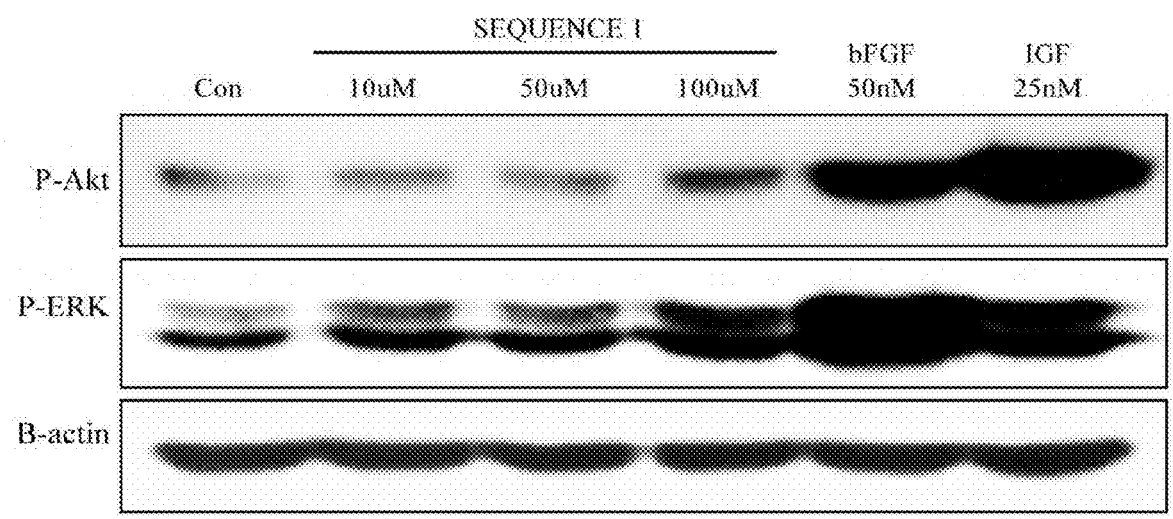
FIG. 6A shows the result of Western blotting that confirms amounts of p-Akt and p-ERK proteins of NIH3T3 cells treated with a peptide including an amino acid sequence of SEQ ID NO: 1.
Figure 6B:
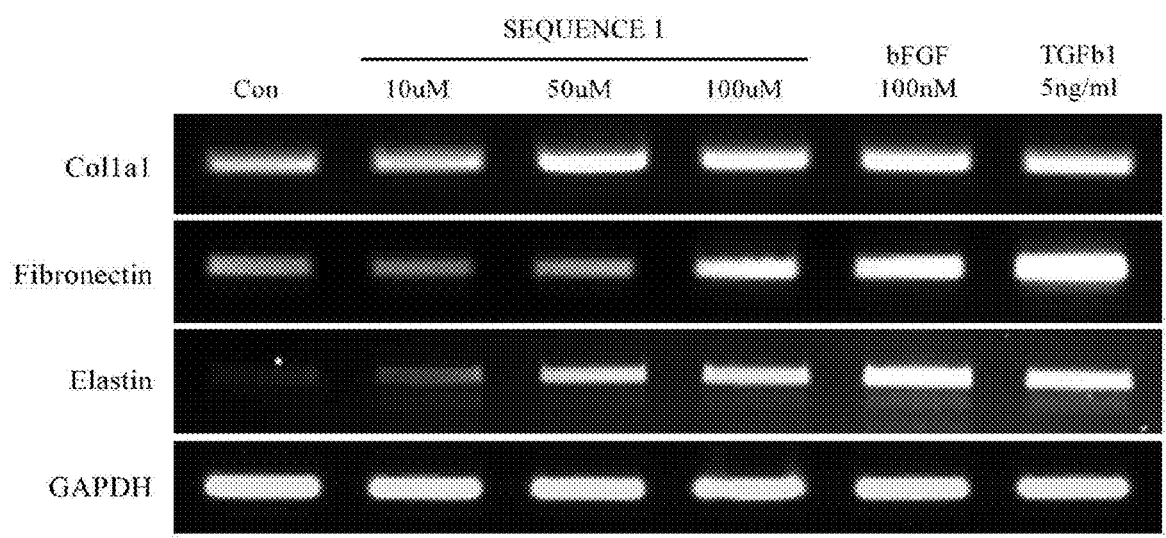
FIG. 6B shows the result of RT-PCR that confirms the expression levels of collagen (Col1a1), fibronectin, and elastin genes of NIH3T3 cells treated with a peptide including an amino acid sequence of SEQ ID NO: 1.

As a result, as shown in the result of the Western blotting of FIG. 6A, it was confirmed that phosphorylation degrees of Akt and ERK gradually increased as the concentration of the peptide increased when the cells were treated with the peptide.

In this regard, the phosphorylation degrees of Akt and ERK in the NIH3T3 cells increased by the peptide including an amino acid sequence of SEQ ID NO: 1, which denotes promotion of growth of the cells, and thus it may be known that a natural aging phenomenon may be suppressed by treating the cells with the peptide.

<6-2> Confirmation of Increase in Expression of Dermal Components (Collagen, Fibronectin, and Elastin)

Whether a cell aging phenomenon may be suppressed by treating the cells with the peptide of the present invention was confirmed by checking whether expression levels of collagen, fibronectin, and elastin genes related to formation of fibers increase, where collagen, fibronectin, and elastin are components that constitute dermis. COL1A1 is a gene encoding collagen I.

26 passages of NIH3T3 cells were seeded in a 6-well plate at a cell density of $3\times10^5$/well and cultured for about 24 hours in a serum free media, and then, the cells were treated with the peptide of the present invention at concentrations of 10 μM, 50 μM, and 100 μM, respectively, for about 24 hours. The positive control was treated with growth factors, 100 nM of bFGF and 5 nM of tgf-β1, respectively, instead of the peptide. After allowing the cells to react with the mixture for about 24 hours, RNA was isolated from the cells in the same manner as in Experimental Example 2, and the isolated RNA was reverse transcribed into cDNA, and RT-PCR (cDNA polymerization kit and PCR pre-mix, available from Intron, Korea) was performed thereon using primers of Col1a1, fibronectin, and elastin (Table 4). A primer of GAPDH having the sequence shown in Table 2 was used for the comparison of the total RNA amounts in each of the control groups.

TABLE 5

| SEQ ID NO: | Sequence name | Nucleotide sequence |
|---|---|---|
| 16 | AQP3 forward | 5'-CCTTCTTGGGTGCTGGAATA-3' |
| 17 | AQP3 reverse | 5'-ACACGATAAGGGAGGCTCTG-3' |

As a result, as shown in the result of RT-PCR of FIG. 7, it was confirmed that expression levels of SIRT1 and AQP3 genes, which was inhibited by the UVB irradiation, gradually increased as the concentration of the peptide increased when the cells were treated with the peptide.

In this regard, it may be known that the expression level of SIRT1, which is an anti-aging gene, and the expression level of AQP3, which is a skin barrier component, that were decreased in the HaCaT cells may increase and recover by the peptide including an amino acid sequence of SEQ ID NO: 1, and thus a photo-aging phenomenon of the cells may be suppressed.

[Experimental Example 8] Confirmation of Activity Recovery of Fibroblasts Suppressed by Photoaging-Inhibiting UV Light <8-1> Confirmation of Expression Recovery of Dermis Components (Collagen, Fibronectin, and Elastin)

When UV is irradiated, the expressions of genes of collagen, fibronectin, and elastin, which are components of the dermis, are inhibited, and thus whether the photoaging phenomenon of the cell may be suppressed or not was checked to confirm whether expression levels of the collagen, fibronectin, and elastin genes recover and increase by treating the cells with the peptide of the present invention.

First, 34 passages of NIH3T3 cells were seeded in a 6-well plate at a cell density of $5\times10^5$/well and cultured for about 16 hours in a serum free media, and then, the cells were treated with the peptide of the present invention at concentrations of 10 μM, 50 μM, and 100 μM, respectively, for about 1 hour. The resultant was washed with PBS, filled with PBS, and pre-irradiated again with 6 J/cm² of UVA for about 1 hour. Then, the cells were treated with the peptide of the present invention at the concentrations above for about 6 hours. The positive control was treated with 2.5 mM of NaC and 50 μM of Quercetin, respectively, instead of the peptide. After allowing the cells to react with the peptide for about 6 hours, RNA was isolated from the cells in the same manner as in Experimental Example 2, and the isolated RNA was reverse transcribed into cDNA, and RT-PCR (cDNA polymerization kit and PCR pre-mix, available from Intron, Korea) was performed thereon using primers of Col1a1, fibronectin, and elastin (Table 4). A primer of GAPDH having the sequence shown in Table 2 was used for the comparison of the total RNA amounts in each of the control groups.

As a result, as shown in the result of RT-PCR of FIG. 8A, it was confirmed that expression levels of the collagen (Col1a1), fibronectin, and elastin genes gradually increased as the concentration of the peptide increased when the cells were treated with the peptide.

In this regard, it may be known that the expression levels of the collagen (Col1a1), fibronectin, and elastin genes, which decreased by the UVA irradiation, in NIH3T3 cells may increase and recover by the peptide including an amino acid sequence of SEQ ID NO: 1, and thus there may be an effect of reducing skin wrinkles by proteins expressed by the genes above as a result of the suppression of the photoaging phenomenon of the cells.

<8-2> Confirmation of Expression Inhibition of MMP-1 and MMP-2

Since expressions of MMP-1 and MMP-2 encoding proteins associated with collagen degradation by UV irradiation, it was confirmed whether a cell aging phenomenon may be suppressed as synthesis of the MMP-1 and MMP-2 proteins is suppressed again when the cells are treated with the peptide of the present invention.

31 passages of NIH3T3 cells were seeded in a 6-well plate at a cell density of $5\times10^5$/well and cultured for about 16 hours in a serum free media, and then, the cells were treated with the peptide of the present invention at concentrations of 10 μM, 50 μM, and 100 μM, respectively, for about 1 hour. The resultant was washed with PBS, filled with PBS, and pre-irradiated again with 6 J/cm² of UVA for about 1 hour. Then, the peptide of the present invention was treated at these concentrations for about 48 hours. The positive control was treated with 2.5 mM of NaC and 50 μM of Quercetin, respectively, instead of the peptide. After allowing the cells to react with the mixture for about 48 hours, a lysate was obtained from the cells, and then Western blotting was performed on MMP-1 using anti-MMP-1 antibody (available from Cell Signaling, USA). 1-actin used in the test was anti-β-actin antibody (available from Santacruz biotechnology, USA) to compare the total amounts of proteins.

Also, in order to analyze an amount of MMP-2, a lysate of the cells obtained was prepared, and then Gelatin zymography was performed on the lysate. Protein electrophoresis (SDS-PAGE) was conducted using gelatin (2 mg/ml) as a substrate. After the electrophoresis, the gel was immersed in 2.5% Triton X-100 for 30 minutes, and then incubated in a buffer containing 50 mM Tris-HCl, 0.2 M NaCl, and 5 mM $CaCl_2$), and 1% Triton X-100 at a temperature of 37° C. for 24 hours. After the incubation, the gel was stained with Coomassie Brilliant Blue R250 (available from Sigma), and then treated with a de-staining buffer containing 5% ethanol, 7.5% acetic acid, and distilled water. Thereafter, empty bands of a gel phase formed by gelatin hydrolysis were observed to confirm activity of MMP-2.

As a result, as shown in the results of Western blotting and zymography of FIG. 8B, it was confirmed that protein amounts of MMP-1 and MMP-2 gradually decreased as the concentrations of the peptide increased when the cells were treated with the peptide.

In this regard, it may be known that the protein amounts of MMP-1 and MMP-2 that have been increased by the UVA irradiation in NIH3T3 cells may be recovered as they decrease again by the peptide including an amino acid sequence of SEQ ID NO: 1, and an amount of collagen may increase again, which has an effect of reducing skin wrinkles as a photoaging phenomenon of the cells is reduced.

As described above, although the present invention has been described in detail with reference to one of more embodiments described herein, it will be apparent to those skilled in the art that various changes and modifications are possible within the scope of the technical concept of the present invention, and it is obvious that such changes and modifications made therein are within the spirit and scope defined by the following claims.

The invention claimed is:

1. A synthetic peptide having activity of inhibiting pollutants from inflow into skin, the synthetic peptide consisting of the amino acid sequence of SEQ ID No: 1, wherein the N-terminus or the C-terminus of the synthetic peptide is linked to a protective group, wherein the synthetic peptide adsorbs pollutants selected from the group consisting of dioxin, particulate matter, and cigarette smoke extract.

2. A pharmaceutical composition for preventing diseases caused by pollutants selected from the group consisting of dioxin, particulate matter, and cigarette smoke extract, the pharmaceutical composition comprising the synthetic peptide of claim 1 as an active ingredient.

3. The pharmaceutical composition of claim 2, wherein the diseases caused by pollutants are at least one selected from the group consisting of atopic dermatitis, contact dermatitis, seborrheic dermatitis, acne, dry skin, psoriasis, immunotoxicity, peripheral nervous system damage, central nervous system damage, endocrine abnormalities, anemia, bronchitis, emphysema, reduced lung function, asthma, and chronic bronchitis.

4. A pharmaceutical composition for improving skin anti-aging, the pharmaceutical composition comprising the synthetic peptide of claim 1 as an active ingredient.

5. The pharmaceutical composition of claim 4, wherein the improving skin anti-aging is reduction of wrinkles.

6. A cosmetic composition for preventing skin damage caused by pollutants or for improving skin anti-aging, the cosmetic composition comprising the synthetic peptide of claim 1 as an active ingredient.

7. The cosmetic composition of claim 6, wherein the cosmetic composition has at least one formulation selected from the group consisting of solution, suspension, emulsion, gel, lotion, essence, cream, powder, soap, shampoo, conditioner, pack mask, surfactant-containing cleanser, cleansing foam, cleansing water, oil, liquid foundation, cream foundation, and spray.

8. A method of treating a disease caused by pollutants selected from the group consisting of dioxin, particulate matter, and cigarette smoke extract in a subject, the method comprising administering the synthetic peptide consisting of the amino acid sequence of SEQ ID NO: 1, wherein the N-terminus or the C-terminus of the peptide is linked to a protective group, to the subject, wherein the diseases caused by pollutants are at least one selected from the group consisting of atopic dermatitis, contact dermatitis, seborrheic dermatitis, acne, dry skin, psoriasis, immunotoxicity, peripheral nervous system damage, central nervous system damage, endocrine abnormalities, anemia, bronchitis, emphysema, reduced lung function, asthma, and chronic bronchitis.

9. A method of improving skin anti-aging, the method comprising administering a synthetic peptide of claim 1 to a subject.

10. The pharmaceutical composition of claim 2, wherein the pharmaceutical composition further comprises a pharmaceutically acceptable carrier, wherein the pharmaceutically acceptable carrier is lipids, liposomes, microspheres, or nano spherical particles.

\* \* \* \* \*